(12) United States Patent
Sturgis et al.

(10) Patent No.: US 11,491,099 B2
(45) Date of Patent: Nov. 8, 2022

(54) ANTIPERSPIRANT AND DEODORANT COMPOSITIONS

(71) Applicant: The Procter & Gamble Company, Cincinnati, OH (US)

(72) Inventors: David Arthur Sturgis, Montgomery, OH (US); Jianjun Justin Li, West Chester, OH (US); Marc Adam Flickinger, West Chester, OH (US); Virginia Tzung-Hwei Hutchins, Cincinnati, OH (US); Steven Louis Diersing, Cincinnati, OH (US); Steven Michael Wujek, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 352 days.

(21) Appl. No.: 15/696,282

(22) Filed: Sep. 6, 2017

(65) Prior Publication Data

US 2018/0064624 A1 Mar. 8, 2018

Related U.S. Application Data

(60) Provisional application No. 62/383,675, filed on Sep. 6, 2016.

(51) Int. Cl.
*A61K 8/73* (2006.01)
*A61K 8/02* (2006.01)
(Continued)

(52) U.S. Cl.
CPC ............ *A61K 8/738* (2013.01); *A61K 8/0229* (2013.01); *A61K 8/046* (2013.01); *A61K 8/28* (2013.01); *A61K 8/34* (2013.01); *A61K 8/347* (2013.01); *A61K 8/37* (2013.01); *A61Q 15/00* (2013.01); *C11B 9/0015* (2013.01);
(Continued)

(58) Field of Classification Search
CPC ....................................................... A61K 8/738
See application file for complete search history.

(56) References Cited

U.S. PATENT DOCUMENTS 4,049,792 A 9/1977 Elsnau
4,731,243 A 3/1988 Lindauer
(Continued)

FOREIGN PATENT DOCUMENTS

EP 0392608 B1 6/1995
EP 1024785 B1 1/2003
(Continued)

OTHER PUBLICATIONS

PCT International Search Report dated Oct. 30, 2017 (12 pages).
(Continued)

*Primary Examiner* — Isaac Shomer
(74) *Attorney, Agent, or Firm* — Kathleen Y Carter

(57) ABSTRACT

An anhydrous stick composition, including deodorant active, an antiperspirant active, or a combination thereof; a carrier; a structurant; and a cyclodextrin perfume complex, comprising cyclodextrin and a perfume, wherein the perfume comprises perfume raw materials and 10% or more, by weight of the perfume, of the perfume raw materials have: a cyclodextrin complex stability constant of about 3.0 or less, a C log P of about 2.5 or less; and a weight average molecular weight of about 200 Daltons or less.

19 Claims, 4 Drawing Sheets

(51) Int. Cl.
| | |
|---|---|
| *A61K 8/34* | (2006.01) |
| *A61K 8/37* | (2006.01) |
| *A61Q 15/00* | (2006.01) |
| *C11B 9/00* | (2006.01) |
| *A61K 8/04* | (2006.01) |
| *A61K 8/28* | (2006.01) |

(52) U.S. Cl.
CPC ........ *C11B 9/0019* (2013.01); *A61K 2800/31* (2013.01); *A61K 2800/56* (2013.01)

(56) References Cited

U.S. PATENT DOCUMENTS

| | | |
|---|---|---|
| 4,803,195 A | 2/1989 | Holzner |
| 4,904,307 A | 2/1990 | Ammeraal |
| 5,094,761 A | 3/1992 | Trinh |
| 5,135,747 A | 8/1992 | Faryniarz |
| 5,176,903 A | 1/1993 | Goldberg |
| 5,378,468 A | 1/1995 | Suffis |
| 5,380,707 A | 1/1995 | Barr |
| 5,403,828 A | 4/1995 | Lewis |
| 5,429,816 A | 7/1995 | Hofrichter et al. |
| 5,508,259 A | 4/1996 | Holzner |
| 5,543,157 A | 8/1996 | Trinh |
| 5,580,851 A | 12/1996 | Trinh |
| 5,626,856 A | 5/1997 | Berndt |
| 5,660,845 A | 8/1997 | Trinh |
| 5,711,941 A | 1/1998 | Behan |
| 5,714,445 A | 2/1998 | Trinh |
| 5,718,887 A | 2/1998 | Wolf et al. |
| 5,723,420 A | 3/1998 | Wei |
| 5,733,272 A | 3/1998 | Brunner |
| 5,780,020 A | 7/1998 | Peterson |
| 5,840,287 A | 11/1998 | Guskey et al. |
| 5,840,289 A | 11/1998 | Hall |
| 5,861,144 A | 1/1999 | Peterson et al. |
| 5,874,067 A | 2/1999 | Lucas |
| 5,879,666 A | 3/1999 | Lucas |
| 5,882,638 A | 3/1999 | Dodd |
| 5,897,854 A | 4/1999 | Lucas |
| 5,897,855 A | 4/1999 | Trinh |
| 5,932,198 A | 8/1999 | Goldman |
| 5,932,199 A | 8/1999 | Esser |
| 5,968,489 A | 10/1999 | Swaile et al. |
| 5,976,514 A | 11/1999 | Guskey |
| 6,013,248 A | 1/2000 | Luebbe et al. |
| 6,036,964 A | 3/2000 | Guenin |
| 6,077,318 A | 6/2000 | Trinh et al. |
| 6,110,449 A | 8/2000 | Bacon et al. |
| 6,123,932 A | 9/2000 | Guskey et al. |
| 6,165,452 A | 12/2000 | Boden |
| 6,180,121 B1 | 1/2001 | Guenin |
| 6,287,603 B1 | 9/2001 | Prasad et al. |
| 6,306,818 B1 | 10/2001 | Anderson |
| 6,352,688 B1 | 3/2002 | Scavone et al. |
| 6,495,097 B1 | 12/2002 | Streit |
| 6,509,010 B2 | 1/2003 | Beck |
| 6,793,915 B1 | 9/2004 | Guenin |
| 6,805,855 B2 | 10/2004 | Mattai |
| 6,824,763 B2 | 11/2004 | Brooks |
| 6,835,373 B2 | 12/2004 | Kolodzik et al. |
| 6,869,923 B1 | 3/2005 | Cunningham |
| 6,893,647 B1 | 5/2005 | Malton et al. |
| 6,936,242 B2 | 8/2005 | Elliott et al. |
| 7,041,337 B2 | 5/2006 | Heltovics et al. |
| 7,208,462 B2 | 4/2007 | Heltovics et al. |
| 7,208,463 B2 | 4/2007 | Heltovics et al. |
| 7,208,464 B2 | 4/2007 | Heltovics et al. |
| 7,208,465 B2 | 4/2007 | Heltovics et al. |
| 7,407,650 B2 | 8/2008 | Heltovics et al. |
| 7,413,731 B2 | 8/2008 | Heltovics et al. |
| 8,147,808 B2 | 4/2012 | Scavone et al. |
| 8,632,755 B2 | 1/2014 | Scavone et al. |
| 9,222,055 B2 | 12/2015 | Fraser |
| 9,649,386 B2 | 5/2017 | Scavone et al. |
| 9,649,387 B2 * | 5/2017 | Scavone ................. A61F 13/15 |
| 10,052,271 B2 * | 8/2018 | Sturgis ................. A61K 8/0216 |
| 10,149,910 B2 | 12/2018 | Scavone |
| 10,351,796 B2 * | 7/2019 | Sturgis ................... A61K 8/738 |
| 11,000,468 B2 * | 5/2021 | Sturgis ..................... A61K 8/44 |
| 2002/0007055 A1 | 1/2002 | Uchiyama et al. |
| 2002/0025946 A1 | 2/2002 | Buchanan |
| 2003/0049290 A1 | 3/2003 | Jha |
| 2003/0060379 A1 | 3/2003 | Souter et al. |
| 2003/0069165 A1 | 4/2003 | Malton et al. |
| 2003/0087776 A1 | 5/2003 | Heltovics |
| 2003/0119713 A1 | 6/2003 | Heltovics |
| 2003/0194416 A1 | 10/2003 | Shefer |
| 2003/0198680 A1 | 10/2003 | Shefer |
| 2003/0211125 A1 | 11/2003 | Heltovics |
| 2003/0232025 A1 | 12/2003 | Colwell |
| 2003/0232730 A1 | 12/2003 | Holland et al. |
| 2004/0001891 A1 | 1/2004 | Smith |
| 2004/0077520 A1 | 4/2004 | Foley |
| 2004/0091435 A1 | 5/2004 | Shefer |
| 2004/0109833 A1 | 6/2004 | Tang |
| 2004/0175404 A1 | 9/2004 | Shefer |
| 2004/0202632 A1 | 10/2004 | Gott |
| 2005/0003975 A1 | 1/2005 | Browne |
| 2006/0159639 A1 | 7/2006 | Ogura |
| 2006/0243322 A1 | 11/2006 | Heltovics et al. |
| 2006/0263236 A1 | 11/2006 | Woo et al. |
| 2006/0263313 A1 | 11/2006 | Scavone |
| 2006/0292098 A1 | 12/2006 | Scavone |
| 2007/0166254 A1 * | 7/2007 | Bianchi ................. A61K 8/0229 424/66 |
| 2007/0248553 A1 | 10/2007 | Scavone et al. |
| 2008/0087776 A1 | 4/2008 | Chuang |
| 2008/0194454 A1 | 8/2008 | Morgan |
| 2008/0213191 A1 | 9/2008 | Scavone et al. |
| 2008/0213203 A1 | 9/2008 | Seavone |
| 2008/0213204 A1 | 9/2008 | Scavone et al. |
| 2008/0215023 A1 | 9/2008 | Scavone et al. |
| 2008/0241201 A1 | 10/2008 | Warr et al. |
| 2009/0010972 A1 | 1/2009 | Modafari et al. |
| 2009/0029020 A1 | 1/2009 | Strassburger |
| 2009/0084513 A1 | 4/2009 | Barnholtz et al. |
| 2009/0214446 A1 | 8/2009 | Strassburger |
| 2009/0218057 A1 | 9/2009 | Manifold et al. |
| 2009/0218058 A1 | 9/2009 | Manifold et al. |
| 2010/0226871 A1 | 9/2010 | Fraser et al. |
| 2011/0183132 A1 | 7/2011 | Manifold et al. |
| 2012/0087828 A1 | 4/2012 | Uchiyama |
| 2013/0302566 A1 | 11/2013 | Barnholtz et al. |
| 2014/0274870 A1 | 9/2014 | Cetti |
| 2018/0064588 A1 | 3/2018 | Sturgis |
| 2018/0064623 A1 | 3/2018 | Sturgis |
| 2018/0064624 A1 | 3/2018 | Sturgis |
| 2018/0066206 A1 | 3/2018 | Horenziak |
| 2018/0066207 A1 | 3/2018 | Sturgis |
| 2019/0292488 A1 | 9/2019 | Sturgis |

FOREIGN PATENT DOCUMENTS

| | | |
|---|---|---|
| EP | 0535942 B2 | 11/2004 |
| JP | S6335517 A | 2/1988 |
| JP | H03259986 A | 11/1991 |
| JP | H10120541 A | 5/1998 |
| JP | H10263062 A | 10/1998 |
| JP | H11209784 A | 8/1999 |
| JP | 2002037722 A | 2/2002 |
| KR | 20150070937 | 6/2015 |
| WO | WO9856340 A1 | 12/1998 |
| WO | 0234227 A1 | 5/2002 |
| WO | WO02069924 A1 | 9/2002 |

OTHER PUBLICATIONS

PCT International Search Report, dated Nov. 28, 2017 (14 pages).
PCT International Search Report, dated Dec. 1, 2017 (12 pages).
Del Valle, E. M. Martin; Cyclodextrins and their uses: a review; Process Biochemistry; vol. 39; 2004; pp. 1033-1046.

(56) References Cited

OTHER PUBLICATIONS

Hedges, Allan R.; Industrial Applications of Cyclodextrins; Chem. Rev. 1998; vol. 98; pp. 2035-2044.
All Office Actions; U.S. Appl. No. 15/696,268, filed Sep. 6, 2017.
All Office Actions; U.S. Appl. No. 15/696,274, filed Sep. 6, 2017.
All Office Actions; U.S. Appl. No. 16/429,683, filed Jun. 3, 2019.

* cited by examiner

ANTIPERSPIRANT AND DEODORANT COMPOSITIONS

CROSS REFERENCE TO RELATED APPLICATION

This application claims the benefit of U.S. Provisional Application No. 62/383,675, filed Sep. 6, 2016, the substance of which is incorporated herein by reference.

FIELD OF THE INVENTION

This application generally relates to antiperspirants and deodorant compositions comprising a cyclodextrin perfume complex.

BACKGROUND OF THE INVENTION

Perfume compositions are utilized to help make products more delightful to consumers. This is especially true for perfume compositions and complexes that can provide a desired and long-lasting perfume or scent each time the composition is applied or used. However, current perfume compositions are not optimized for release from a cyclodextrin complex and some components can remain within the complex and unexpressed. As such, there is a need for a perfume composition which is optimized for release from a cyclodextrin and cyclodextrin perfume complexes made from such optimized perfumes.

SUMMARY OF THE INVENTION

Included herein, for example, is an anhydrous stick composition, comprising a deodorant active, an antiperspirant active, or a combination thereof; a carrier; a structurant; and a cyclodextrin perfume complex, wherein the cyclodextrin perfume complex comprises a cyclodextrin and a perfume comprising perfume raw materials and wherein 10% or more, by weight of the perfume, of the perfume raw materials have: a) a cyclodextrin complex stability constant of about 3.0 or less, b) a C log P of about 2.5 or less; and c) a weight average molecular weight of about 200 Daltons or less.

Also included herein, for example, is an anhydrous stick composition, comprising a deodorant active, an antiperspirant active, or a combination thereof; a carrier; a structurant; and a cyclodextrin perfume complex, wherein the cyclodextrin perfume complex comprises a cyclodextrin and a perfume comprising perfume raw materials and wherein 20% or more, by weight of the perfume, of the perfume raw materials, are selected from the group consisting of: ethyl-2-methyl butyrate; beta gamma hexanol; iso amyl acetate; amyl acetate; cis-3-hexenyl acetate; gamma-octalactone; ethyl vanillin; vanillin; benzaldehyde; dimethyl anthranilate; iso-eugenyl acetate; canthoxal; 3,6-nonadien-1-ol, triplal; and combinations thereof.

These and other combinations are possible and are described in more detail below.

DETAILED DESCRIPTION OF THE INVENTION

Figure 1:
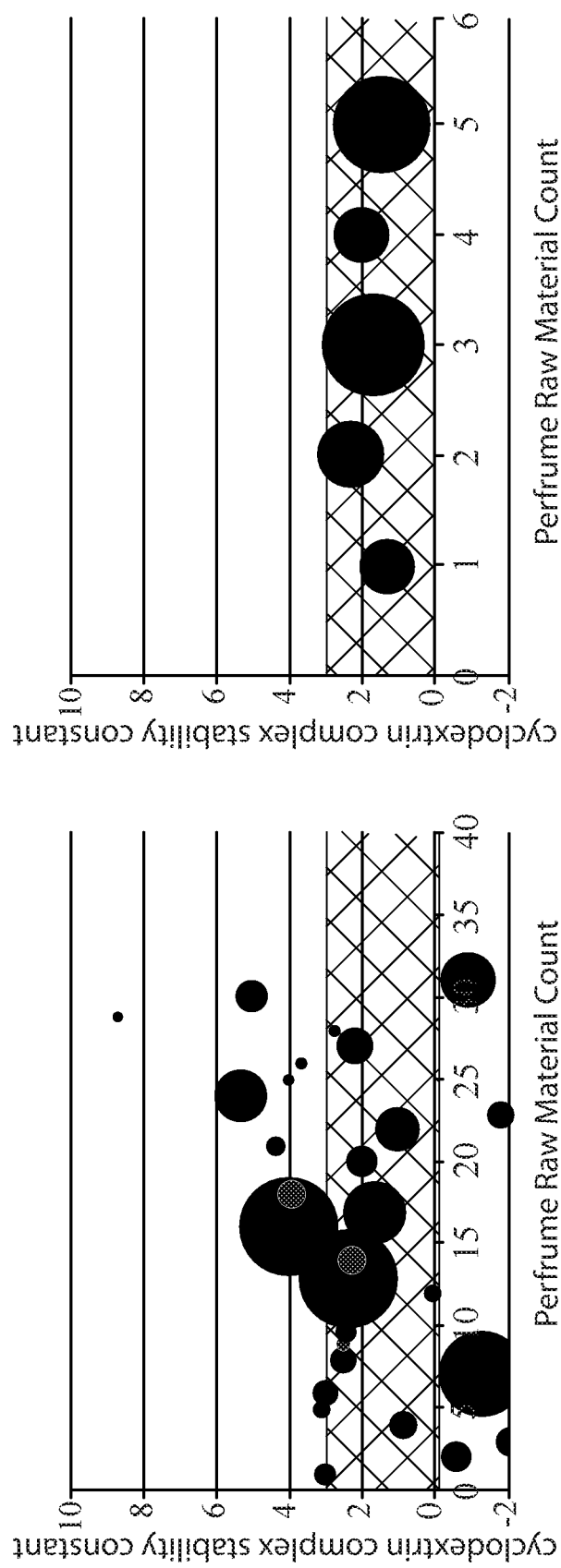
FIG. 1 is a side-by-side comparison of the cyclodextrin complex stability constant (BCD binding strength) of a perfume composition before and after optimization for release from a cyclodextrin complex.

"Anhydrous" refers to a composition that comprises less than about 3% of free or added water, by weight of the composition.

"Cyclodextrin complex stability constant" or "complex stability constant" (log K) refers to the ability of a perfume raw material to bind to a cyclodextrin. The complex stability constant of a multitude of materials with respect to various cyclodextrins as measured by the calorimetry technique can be found in the literature, for example, Rekharsky and Inoue (1998), Complexation Thermodynamics of Cyclodextrins, Chemical Review, 98, 1875-1917. In addition, for reference, a list of perfume raw materials and their estimated complex stability constants is included in a table below.

"C log P" refers to calculated log P values, which is a measure of a compound's hydrophilicity, wherein log P is the octanol water partitioning coefficient as computed by the Consensus algorithm implemented in ACD/Percepta version 14.02 by Advanced Chemistry Development, Inc. (ACD/Labs, Toronto, Canada).

"Odor Detection Threshold" refers to the lowest concentration in the air of a certain odor compound that is perceivable to the human sense of smell. The Odor detection Threshold of a multitude of materials can be found in van Gernert, L. J.; *Odour Thresholds* (*Compilations of Odour Threshold Values in Air, Water and Other Media*; Oliemans Punter & Partners; The Netherlands, 2011. It is in units of -log molar concentration. In this context, human odor detection thresholds (ODTs) are expressed as olfactory power, or p·ol (the negative log of the molar concentration of the odorant in air at which a human first detects the presence of the odorant). These values can be directly transposed to other commonly used units such as ppm (volume) and ppb (volume): thresholds of 1 ppm and 1 ppb are equivalent to p·ol=6 and p·ol=9, respectively. Odor Detection Threshold can be measured, for example, by the method in International Publication Number WO 2006/138726.

"Cyclodextrin complex" refers to a complex of cyclodextrin and perfume.

"Molecular weight," unless otherwise designated, refers to the weight average molecular weight which can be calculated by using the sum of the molecular weights of the elements in a molecule. These can be found, for example, in *Atomic Weights of the Elements*, Weiser, 2005.

"Room temperature as used herein refers to about 20° C.

Many consumers enjoy a good scent in a consumer product. Scent can be delivered through a multitude of means, like direct addition of a scent to a product or through the use of a scent delivery agent. Scent delivery agents can enhance and/or change the delivery of the scent. For example, some delivery agents can encapsulate a perfume so that it can be released upon a triggering event. Other delivery agents can help a perfume deposit onto a target surface so that the perfume is more easily detected by the consumer.

Perfumes are usually not a single component, but made up of multiple perfume raw materials which combined give the overall scent of the perfume. Each of the perfume raw materials has its own characteristic and its own chemical properties, like molecular weight, c Log P, etc. These properties can influence where and how long a scent can be detected. Some of these properties are how perfume raw materials are divided into top, middle, and base notes.

Previously, when using a perfume in combination with a delivery agent like a cyclodextrin, it was believed that most of the perfume was released from the delivery agent upon the triggering event. For cyclodextrins, the triggering event is usually the introduction of moisture. However, it was recently discovered that only about 4%, of a complexed perfume, was being released from a "high" performing cyclodextrin perfume complex upon exposure to moisture. Thus, surprisingly, most of the perfume was remaining within the cyclodextrin and was not noticeable to the consumer. This means there is significant room for improvement in the efficacy of cyclodextrin perfume complexes.

Figure 3:
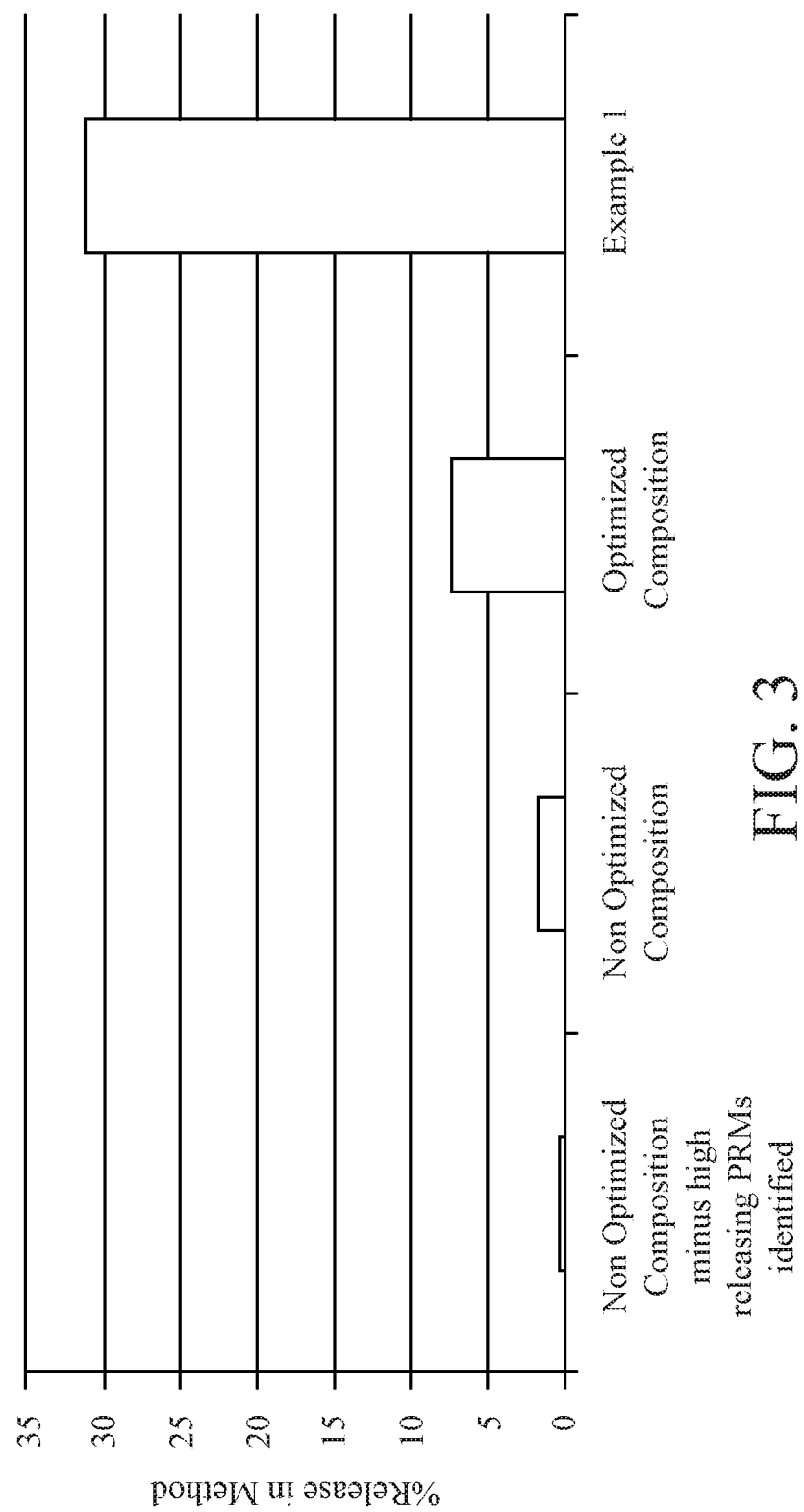
FIG. 3 is a graph showing the percentage of perfume complexed with a beta cyclodextrin that is released when measured in accordance with the In Vitro Perfume Release Method.

An understanding of what is and what isn't releasing from a cyclodextrin was thought helpful to improve the efficacy of the perfume cyclodextrin complex. Since less than 5% of the perfume compositions used in a cyclodextrin complex were efficiently releasing from the cyclodextrin complex (see FIG. 3, Non Optimized Composition), the perfume raw materials that were being release from the cyclodextrins were identified to determine if there were characteristics common among them which could be used to help develop a perfume composition for optimized released from a cyclodextrin.

With water being the key releasing agent, it was found that perfume materials with more affinity with water (lower log P) had better release from the cyclodextrin complex. Perfume materials with a lower cyclodextrin complex stability constant (log k) also had better release from a cyclodextrin complex. In addition, a lower molecular weight, which may correlate with a lower cyclodextrin complex stability constant, also correlates with a better release. To demonstrate these characteristics as impacting the release from the cyclodextrin composition, new perfume compositions were created. One composition removed these higher releasing perfume materials from the original low release composition as a negative control check (see FIG. 3, Non Optimized Composition minus high releasing PRM's identified vs. Non Optimized Composition). These compositions were then complexed with a beta cyclodextrin and tested for release. In release testing, the Non Optimized Composition minus the high releasing PRM's had less than one third of the release of the original Non Optimized Composition (see FIG. 3). This helped confirm which materials were releasing from the cyclodextrin complex.

An optimized composition was also made which utilized about 70%, by weight of the perfume composition, of perfume raw materials with a log P, stability constant, and weight average molecular weight believed to help with perfume release from a cyclodextrin complex. This perfume, Optimized Composition from FIG. 3, had 4 times the release of the original composition (Non Optimized Composition). Another perfume composition was made with 100% of the perfume composition matching these physical property characteristics (Example 1). This perfume composition had over 15 times the release of the Non Optimized Composition.

As noted above, one of the characteristics of a perfume raw material that can impact its release from a cyclodextrin is its complex stability constant. This signifies how strongly the perfume raw material binds with the cyclodextrin. While a minimum complex stability constant allows for a perfume raw material to bind and stay bound, at some point the affinity of the perfume raw material for the cyclodextrin can become so strong that it becomes difficult to release. It is believed that a complex stability constant of more than 3 can interfere with the release of the perfume raw material upon a triggering event. This is not to say that perfume raw materials with a complex stability constant above a 3 cannot be used, just that the ability to release such materials should be taken into consideration during perfume design. For example, FIG. 1 shows the binding complex of perfume raw materials in a perfume composition. The graph on the left shows the make-up of a more typical perfume, while the graph on the right shows a perfume composition after optimization for release from a cyclodextrin. The optimized formula showed an improvement of more than 15 times over Non Optimized Perfume A.

Figure 2:
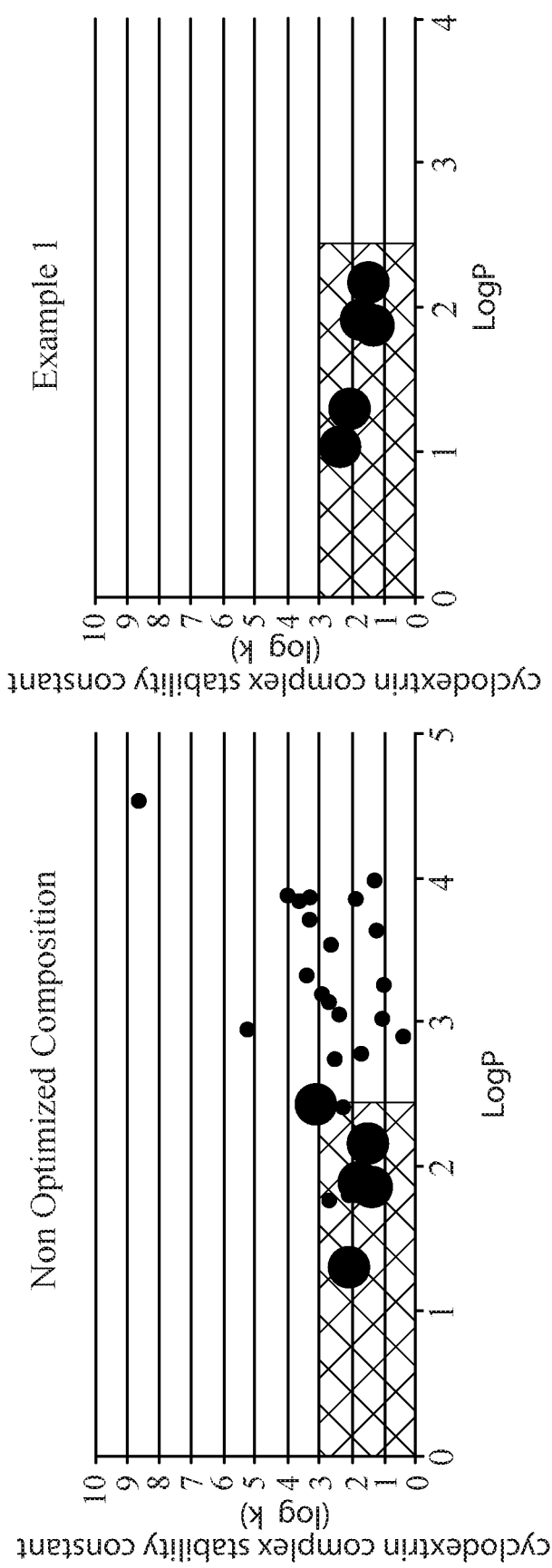
FIG. 2 is a side-by-side comparison of the cyclodextrin complex stability constant over Log P of a perfume composition before and after optimization for release from a cyclodextrin complex.

Another property of a perfume raw material which can impact its ability to release from a cyclodextrin is its C log P. C log P is the calculation of the log P value of a compound, which is the logarithm of its partition coefficient between n-octanol and water ($C_{octanol}/C_{water}$). Thus log P, or if calculated, c Log P, is a measure of a perfume raw material's hydrophilicity. High log P values correspond to low hydrophilicities. It is believed that a low log P, i.e. higher affinity for water, can positively impact the release of a perfume raw material from a cyclodextrin upon appropriate contact with moisture. For example, FIG. 2 shows the binding complex of perfume raw materials in a perfume and the C log P. The graph on the left shows the make-up of a more typical perfume, while the graph on the right shows a perfume composition after optimization for release from a cyclodextrin. The optimized formula complexed with a beta cyclodextrin showed an improvement of 15 times over the Non Optimized Composition. For this application, it is believed a C log P value of about 2.5 or less is optimal for release from a cyclodextrin complex.

A third property that can impact the release of a perfume raw material from a cyclodextrin is its weight average molecular weight. It is believed that perfume raw materials which are smaller in size will have less binding points to a cyclodextrin and thus more easily released. Ideally, a perfume raw material for optimal release will have a weight average molecular weight of about 200 Daltons or less.

A fourth property that can impact the need for efficacy is the odor detection threshold. Odor detection threshold is the minimum level at which a perfume raw material can be detected by the average human nose. For a perfume raw material with a low odor detection threshold, less of the perfume raw material needs to be released from a cyclodextrin in order for the perfume raw material to be noticed. This feature can allow for the use of perfume raw materials which would otherwise be seen as too difficult to release en masse from a cyclodextrin as only a small amount of release can be noticeable to a consumer. Optimally, the odor detection threshold of a perfume raw material is about 7-log molar concentration or more.

Figure 4:
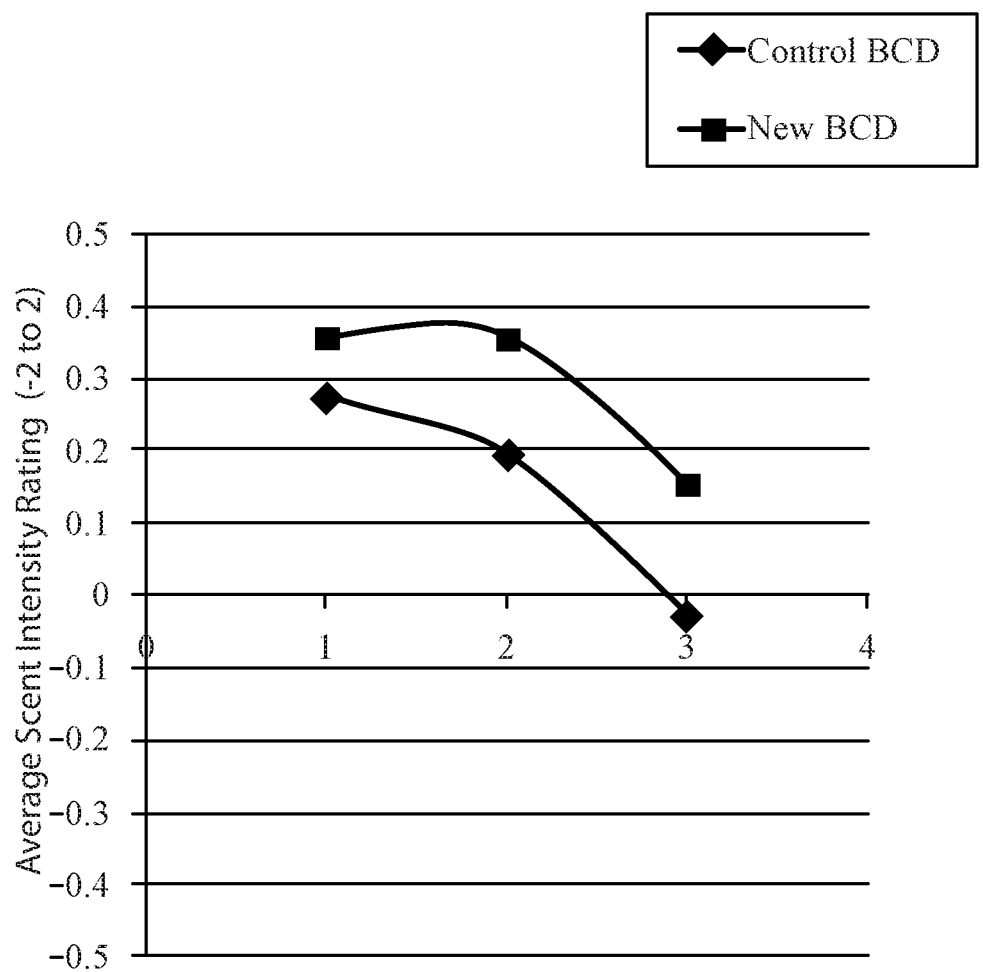
FIG. 4 is a graph showing the average scent intensity at each assessment time point, where 1 is at application, 2 is during the day, and 3 is at the end of the day.

To determine whether the release enhancement was noticeable to consumers, an optimized beta cyclodextrin perfume complex was placed into an invisible solid antiperspirant product and was tested against an in market beta cyclodextrin complex with less than 5% release in a similar product. The products were given to over 90 consumers each to wear every day for 2 weeks. After the 2 weeks they were asked to rate the intensity of the perfume on a scale of −2 (much too weak) to 2 (much too strong). They rated the product they wore at application, during the day, and at the end of the day. FIG. 4 shows on average those who wore the product with the optimized cyclodextrin reported a higher perfume intensity at each time point evaluated. With the single variable change of the perfume in the cyclodextrin perfume complex between the two test products, we believe the increase in fragrance intensity can be attributed to the optimized perfume in the cyclodextrin perfume complex.

Antiperspirant/Deodorant Composition

A deodorant or antiperspirant composition may include an active, a carrier, a structurant, and a cyclodextrin perfume complex. The active may be a deodorant active, an antiperspirant active, or a combination thereof. Antiperspirant and deodorant compositions can be, for example, in the form of a stick and either a soft solid or a solid. Soft solid forms can generally be delivered through perforated domes, while solids are utilized without a dome for delivery. The composition can be anhydrous.

Deodorant Active

Suitable deodorant actives can include any topical material that is known or otherwise effective in preventing or eliminating malodor associated with perspiration. Suitable deodorant actives may be selected from the group consisting of antimicrobial agents (e.g., bacteriocides, fungicides), malodor-absorbing material, and combinations thereof. For example, antimicrobial agents may comprise cetyl-trimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmethyl sarcosine, lauroyl sarcosine, N-myristoyl glycine, potassium N-lauryl sarcosine, trimethyl ammonium chloride, sodium aluminum chlorohydroxy lactate, triethyl citrate, tricetylmethyl ammonium chloride, 2,4,4'-trichloro-2'-hydroxy diphenyl ether (triclosan), 3,4,4'-trichlorocarbanilide (triclocarban), diaminoalkyl amides such as L-lysine hexadecyl amide, heavy metal salts of citrate, salicylate, and piroctose, especially zinc salts, and acids thereof, heavy metal salts of pyrithione, especially zinc pyrithione, zinc phenolsulfate, farnesol, and combinations thereof. The concentration of the deodorant active may range from about 0.001%, from about 0.01%, of from about 0.1%, by weight of the composition to about 20%, to about 10%, to about 5%, or to about 1%, by weight of the composition.

Antiperspirant Active

The compositions can include an antiperspirant active suitable for application to human skin. The concentration of the antiperspirant active in the antiperspirant composition should be sufficient to provide the desired enhanced wetness protection. For example, the active can be present in an amount of from about 0.1%, about 0.5%, about 1%, or about 5%; to about 60%, about 35%, about 25% or about 20%, by weight of the antiperspirant composition. These weight percentages are calculated on an anhydrous metal salt basis exclusive of water and any complexing agents such as glycine, glycine salts, or other complexing agents.

An antiperspirant active can include any compound, composition, or other material having antiperspirant activity. Such actives can include astringent metallic salts, like inorganic and organic salts of aluminum, zirconium and zinc, as well as mixtures thereof. For example, the antiperspirant active can include zirconium-containing salts or materials, such as zirconyl oxyhalides, zirconyl hydroxyhalides, and mixtures thereof; and/or aluminum-containing salts such as, for example, aluminum halides, aluminum chlorohydrate, aluminum hydroxyhalides, and mixtures thereof.

1. Aluminum Salts

Aluminum salts useful herein can include those that conform to the formula:

$$Al_2(OH)_aCl_b \cdot xH_2O$$

wherein a is from about 2 to about 5; the sum of a and b is about 6; x is from about 1 to about 6; where a, b, and x can have non-integer values. For example, aluminum chlorohydroxides referred to as "5/6 basic chlorohydroxide," wherein a is about 5 and "2/3 basic chlorohydroxide", wherein a=4 can be used.

A general description of these aluminum salts can be found in Antiperspirants and Deodorants, Cosmetic Science and Technology Series Vol. 20, 2nd edition, edited by Karl Laden. Mixtures of aluminum salts are described in British Patent Specification 1,347,950, filed in the name of Shin et al. and published Feb. 24, 1974.

2. Zirconium Salts

Zirconium salts useful herein can include those which conform to the formula:

$$ZrO(OH)_{2-a}Cl_a \cdot xH_2O$$

wherein a is from about 1.5 to about 1.87; x is from about 1 to about 7; and wherein a and x can both have non-integer values. These zirconium salts are described in Belgian Patent 825,146, issued to Schmitz on Aug. 4, 1975. Useful to the present invention are zirconium salt complexes that additionally contain aluminum and glycine, commonly known as "ZAG complexes". These complexes can contain aluminum chlorohydroxide and zirconyl hydroxy chloride conforming to the above-described formulas. Examples of two such complexes include aluminum zirconium trichlorohydrex and aluminum zirconium tetrachlorohydrex.

The antiperspirant active can comprise, for example, aluminum zirconium tetrachlorohydrex glycine; aluminum zirconium tetrachlorohydrate, aluminum zirconium pentachlorohydrate, aluminum zirconium pentachlorohydrex glycine, aluminum zirconium trichlorohydrex glycine, aluminum zirconium trichlorohydrate, aluminum zirconium octachlorohydrate, aluminum zirconium octachlorohydrex glycine, aluminum chlorohydrate, aluminum chlorohydrex polyethylene glycol, aluminum dichlorohydrate, aluminum dichlorohydrex polyethylene glycol, aluminum dichlorohydrex propylene glycol, aluminum sesquichlorohydrate, aluminum sesquichlorohydrex polyethylene glycol, aluminum sesquichlorohydrex propylene glycol or a combination thereof.

Carrier

The composition can also include a carrier. The carrier can be present, for example, at concentrations ranging from about 10%, about 15%, about 20%, about 25%; to about 99%, about 70%, about 60%, or about 50%, by weight of the composition. Such concentrations will vary depending upon variables such as product form, desired product hardness, and selection of other ingredients in the antiperspirant composition. The carrier can be any anhydrous carrier known for use in antiperspirant or deodorant compositions or otherwise suitable for topical application to the skin. For example, anhydrous carriers can include, but are not limited to, volatile and nonvolatile fluids.

A. Volatile Fluid

The compositions can also include a volatile fluid such as a volatile silicone carrier. Volatile fluids are present, for example, at concentrations ranging from about 20% or from about 30%; to about 80%, or no about 60%, by weight of the composition. The volatile silicone of the solvent can be cyclic, linear, and/or branched chain silicone. "Volatile silicone", as used herein, refers to those silicone materials that have measurable vapor pressure under ambient conditions. Non-limiting examples of suitable volatile silicones are described in Todd et al., "Volatile Silicone Fluids for Cosmetics", Cosmetics and Toiletries, 91:27-32 (1976).

The volatile silicone can be a cyclic silicone. The cyclic silicone can have from about 3 silicone atoms, or from about 5 silicone atoms; to about 7 silicone atoms, or to about 6 silicone atoms. For example, volatile silicones can be used which conform to the formula:

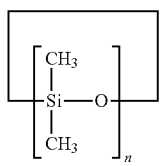

wherein n is from about 3, or from about 5; to about 7, or to about 6. These volatile cyclic silicones generally have a viscosity of less than about 10 centistokes at 25° C. Suitable volatile silicones for use herein include, but are not limited to, Cyclomethicone D5 (commercially available from G. E. Silicones); Dow Corning 344, and Dow Corning 345 (commercially available from Dow Corning Corp.); and GE 7207, GE 7158 and Silicone Fluids SF-1202 and SF-1173 (available from General Electric Co.). SWS-03314, SWS-03400, F-222, F-223, F-250, F-251 (available from SWS Silicones Corp.); Volatile Silicones 7158, 7207, 7349 (available from Union Carbide); Masil SF-V (available from Mazer) and combinations thereof.

B. Non-Volatile Fluid

A non-volatile fluid can also be present, for example, at concentrations ranging from about 1%, from about 2%; to about 20%, or about 15%, by weight of the composition.

1. Non-Volatile Organic Fluids

The non-volatile organic fluid can be present at concentrations ranging from about 1%, from about 2% but no more than about 20% or no more than about 15%, by weight of the composition.

Non-limiting examples of nonvolatile organic fluids include, but are not limited to, mineral oil, PPG-14 butyl ether, isopropyl myristate, petrolatum, butyl stearate, cetyl octanoate, butyl myristate, myristyl myristate, C12-15 alkyl-benzoate (e.g., Finsolv™), dipropylene glycol dibenzoate, PPG-15 stearyl ether benzoate and blends thereof (e.g. Finsolv TPP), neopentyl glycol diheptanoate (e.g. Lexfeel 7 supplied by Inolex), octyldodecanol, isostearyl isostearate, octododecyl benzoate, isostearyl lactate, isostearyl palmitate, isononyl/isononoate, isoeicosane, octyldodecyl neopentanate, hydrogenated polyisobutane, and isobutyl stearate. Many such other carrier liquids are disclosed in U.S. Pat. No. 6,013,248 (Luebbe et al.) and U.S. Pat. No. 5,968,489 (Swaile et al.).

2. Nonvolatile Silicone Fluids

The composition can also include a non-volatile silicone fluid. The non-volatile silicone fluid can be a liquid at or below human skin temperature, or otherwise in liquid form within an antiperspirant composition, like an anhydrous antiperspirant composition, during or shortly after topical application. The concentration of the non-volatile silicone can be from about 1%, from about 2%; to about 15%, about 10%, by weight of the composition. Nonvolatile silicone fluids can include those which conform to the formula:

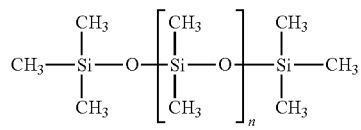

wherein n is greater than or equal to 1. These linear silicone materials can generally have viscosity values of from about 5 centistokes, from about 10 centistokes; to about 100,000 centistokes, about 500 centistokes, about 200 centistokes, or about 50 centistokes, as measured under ambient conditions.

Specific non limiting examples of suitable nonvolatile silicone fluids include Dow Corning 200, hexamethyldisiloxane, Dow Corning 225, Dow Corning 1732, Dow Corning 5732, Dow Corning 5750 (available from Dow Corning Corp.); and SF-96, SF-1066 and SF18(350) Silicone Fluids (available from G.E. Silicones).

Low surface tension non-volatile solvent can be also be used. Such solvents can be selected from the group consisting of dimethicones, dimethicone copolyols, phenyl trimethicones, alkyl dimethicones, alkyl methicones, and mixtures thereof. Low surface tension non-volatile solvents are also described in U.S. Pat. No. 6,835,373 (Kolodzik et al.).

Structurants

Antiperspirant or deodorant compositions can also include a structurant to help provide the composition with the desired viscosity, rheology, texture and/or product hardness, or to otherwise help suspend any dispersed solids or liquids within the antiperspirant composition. The term "structurant" can include any material known or otherwise effective in providing suspending, gelling, viscosifying, solidifying, or thickening properties to the composition or which otherwise provide structure to the final product form. Non-limiting examples of structurants include, for example, gelling agents, polymeric or nonpolymeric agents, inorganic thickening agents, or viscosifying agents. Non-limiting examples of thickening agents include, for example, organic solids, silicone solids, crystalline or other gellants, inorganic particulates such as clays or silicas, or combinations thereof.

The concentration and type of the structurant selected for use in the antiperspirant composition can vary depending upon the desired product form, viscosity, and hardness. The thickening agents suitable for use herein, can have a concentration range from about 0.1%, about 3%, or about 5%; to about 35%, about 20%, or about 10%, by weight of the composition. Soft solids will often contain a lower amount of structurant than solid compositions. For example, a soft solid can contain from about 1.0% to about 9%, by weight of the composition, while a solid composition can contain from about 15% to about 25%, by weight of the antiperspirant composition, of a structurant. This is not a hard and fast rule, however, as a soft solid product with a higher structurant value can be formed by, for example, shearing the product as it is dispensed from a package.

Non-limiting examples of suitable gelling agents include fatty acid gellants, salts of fatty acids, hydroxyl acids, hydroxyl acid gellants, esters and amides of fatty acid or hydroxyl fatty acid gellants, cholesterolic materials, dibenzylidene alditols, lanolinolic materials, fatty alcohols, triglycerides, sucrose esters such as SEFA behenate, inorganic materials such as clays or silicas, other amide or polyamide gellants, and mixtures thereof. Optionally, the microcapsules can be premixed with such gellants prior to incorporation into the antiperspirant composition.

Suitable gelling agents include fatty acid gellants such as fatty acid and hydroxyl or alpha hydroxyl fatty acids, having from about 10 to about 40 carbon atoms, and ester and amides of such gelling agents. Non-limiting examples of such gelling agents include, but are not limited to, 12-hydroxystearic acid, 12-hydroxylauric acid, 16-hydroxyhexadecanoic acid, behenic acid, eurcic acid, stearic acid, caprylic acid, lauric acid, isostearic acid, and combinations thereof. Preferred gelling agents are 12-hydroxystearic acid, esters of 12-hydroxystearic acid, amides of 12-hydroxystearic acid and combinations thereof.

Other suitable gelling agents include amide gellants such as di-substituted or branched monoamide gellants, monsubstituted or branched diamide gellants, triamide gellants, and combinations thereof, including n-acyl amino acid derivatives such as n-acyl amino acid amides, n-acyl amino acid esters prepared from glutamic acid, lysine, glutamine, aspartic acid, and combinations thereof. Other suitable amide gelling agents are described in U.S. Pat. No. 5,429,816, issued Jul. 4, 1995, and U.S. Pat. No. 5,840,287, filed Dec. 20, 1996.

Still other examples of suitable gelling agents include fatty alcohols having at least about 8 carbon atoms, at least about 12 carbon atoms but no more than about 40 carbon atoms, no more than about 30 carbon atoms, or no more than about 18 carbon atoms. For example, fatty alcohols include but are not limited to cetyl alcohol, myristyl alcohol, stearyl alcohol and combinations thereof.

Non-limiting examples of suitable tryiglyceride gellants include tristearin, hydrogenated vegetable oil, trihydroxysterin (Thixcin® R, available from Rheox, Inc.), rape seed oil, castor wax, fish oils, tripalmitin, Syncrowax® HRC and Syncrowax® HGL-C(Syncrowax® available from Croda, Inc.).

Other suitable thickening agents include waxes or wax-like materials having a melt point of above 65° C., more typically from about 65° C. to about 130° C., examples of which include, but are not limited to, waxes such as beeswax, carnauba, bayberry, candelilla, montan, ozokerite, ceresin, hydrogenated castor oil (castor wax), synthetic waxes and microcrystalline waxes. The synthetic wax can be, for example, but not limited to, a polyethylene, a polymethylene, or a combination thereof. Some suitable polymethylenes can have a melting point from about 65° C. to about 75° C. Examples of some suitable polyethylenes include those with a melting point from about 60° C. to about 95° C. Other high melting point waxes are described in U.S. Pat. No. 4,049,792, Elsnau, issued Sep. 20, 1977.

Further structurants for use in the antiperspirant compositions can include inorganic particulate thickening agents such as clays and colloidal pyrogenic silica pigments. For example, but not limited to, colloidal pyrogenic silica pigments such as Cab-O-Sil®, a submicroscopic particulated pyrogenic silica can be used. Other known or otherwise effective inorganic particulate thickening agents that are commonly used in the art can also be used in the antiperspirant compositions described herein. Concentrations of particulate thickening agents can range, for example, from about 0.1%, about 1%, or about 5%; to about 35%, about 15%, about 10% or about 8%, by weight of the composition.

Clay structurants include montmorillonite clays, non-limiting examples of which include bentonites, hectorites, and colloidal magnesium aluminum silicates. These and other clays can be hydrophobically treated, and when treated will generally be used in combination with a clay activator. Non-limiting examples of suitable clay activators include propylene carbonate, ethanol, and combinations thereof. When clay activators are present, the amount of clay activator can be in a range of from about 40%, about 25%, or about 15%; to about 75%, about 60%, or about 50%, by weight of the clay.

Cyclodextrin

A cyclodextrin may be used for substantially "hiding" a perfume material until a triggering mechanism has occurred, such as, for example, perspiration, urination, or menstruation, to "release" the perfume material. As used herein, the term "cyclodextrin" includes any of the known cyclodextrins such as unsubstituted cyclodextrins containing from about six to about twelve glucose units, especially alpha-cyclodextrin, beta-cyclodextrin, gamma-cyclodextrin, and/ or mixtures thereof. For example, cyclodextrins may be selected from the group consisting of beta-cyclodextrin, hydroxypropyl alpha-cyclodextrin, hydroxypropyl beta-cyclodextrin, methylated-alpha-cyclodextrin, methylated-beta-cyclodextrin, and mixtures thereof. Cyclodextrin complexes may be included within a product from at least about 0.1%, from about 1%, from about 2%, or from about 3%; to about 25%, to about 20%, to about 15% or to about 10%, by weight of the composition.

Cyclodextrin particles and cyclodextrin complexes comprising a perfume can be formed by various methods. For example, a solvent (e.g., water), unloaded cyclodextrin particles, and a perfume material can be placed into a container and then mixed for a period of time to permit loading of perfume molecules into "cavities" of cyclodextrin molecules. The mixture may or may not be processed further; e.g., processed through a colloid mill and/or homogenizer. The solvent is then substantially removed, like by drying, from the resulting mixture or slurry to yield cyclodextrin complex particles. Different manufacturing techniques may however impart different particle/complex characterizations, which may or may not be desirable in the product. The particles and/or complexes can have a low level of moisture prior to their inclusion into a product. For example, some may have a moisture level of less than about 20% by weight of the particles, less than about 10% by weight of the particles, or even less than about 6% by weight of the particles, prior to the inclusion of the volume of particles or complexes into a composition. Other moisture levels may also be suitable.

Spray drying a slurry or mixture of cyclodextrin-perfume complexes is one manufacturing technique capable of producing the cyclodextrin particles and cyclodextrin complexes having the above-noted, low moisture levels. Table I below provides a comparison of spray dried cyclodextrin complexes versus complexes formed via an extruder process (kneading).

TABLE I

| Cyclodextrin Complex Moisture Level | |
|---|---|
| Sample | % Moisture |
| Spray Dry Process Sample A | 4.4 |
| Spray Dry Process Sample B | 3.7-4.5 |
| Spray Dry Process Sample C | 5.3 |
| Extruder Process Sample A | 27.87 |
| Extruder Process Sample B | 27.97 |
| Extruder Process Sample C | 24.00 |

Water content, USP (United States Pharmacopeia, current as of Aug. 1, 2006) <921> Method I is the analytical method for determining cyclodextrin complex moisture level, as shown in Table I.

As one can see from Table 1, the moisture level directly manifested by these two methods is dramatically different. It should be understood that this comparison is not intended to disclaim kneading/extruder processes from appended claims that do not specify a particular complex formation process. Rather, a kneading and extrusion method, or other method forming particles/complexes with higher than desired moisture levels, could utilize additional processing after their initial formation. For example, extruded complexes may be processed through an oven or dryer, or exposed to a controlled environment for a period of time.

Although not wishing to be bound by theory, it is believed that cyclodextrin particles/complexes having a relatively high moisture level have an increased tendency to agglomerate. The agglomerated particles may reach a size so as to become perceptible by a consumer; that is, a consumer may characterize the composition as being "gritty." A "gritty" composition may not be desirable to some consumers. Microbial growth is another potential disadvantage associated with employing cyclodextrin particles/complexes with relatively high moisture levels into a final composition depending on the remaining ingredients of the composition and/or storage parameters.

The efficiency or level of complexing with a perfume material is another parameter of cyclodextrin complexes that can vary greatly depending on the manufacturing techniques employed. Put another way, the percent of perfume material that is associated with the interior of a cyclodextrin molecule compared to the percent of perfume material that is associated with the exterior of the cyclodextrin complex. The perfume material that is on the exterior region of the complex is essentially free to be expressed without the requirement of a triggering mechanism. The probability that a consumer perceives the perfume material prior to a triggering mechanism increases as the level of free perfume increases. And perception of a perfume material prior to a triggering mechanism may not be desired depending on the overall composition design and targeted benefit associated with employment of the cyclodextrin complexes. The percent of perfume material that is complexed with cyclodextrin can be, for example, greater than about 75%, in some instances greater than about 90%, and in other instances greater than about 95%. It should be understood that these levels of perfume complexation are directly associated with the complex formation process itself; the percentages do not represent a formulation design of adding a first percentage of perfume material via a cyclodextrin complex and adding a second percentage of neat perfume material.

Spray drying a slurry or mixture of cyclodextrin-perfume complexes is one manufacturing technique capable of producing cyclodextrin complexes having the above-noted levels of perfume complexation. Table II below provides a comparison of spray dried cyclodextrin complexes versus complexes formed via an extruder process (kneading).

TABLE II

Percent of Perfume Loading in Cyclodextrin Complexes

| Sample | Complexation Efficiency |
|---|---|
| Spray Dry Process Sample A | 96.6 |
| Spray Dry Process Sample B | 96.8 |
| Spray Dry Process Sample C | 96.2 |
| Extruder Process Sample A | 60.77 |
| Extruder Process Sample B | 65.47 |
| Extruder Process Sample C | 67.07 |

One can see from Table II that spray drying is capable of producing cyclodextrin complexes with very little free perfume as compared to a kneading/extruder process. The skilled artisan should appreciate that the comparison provided in Table II is not intended to disclaim kneading/extruder processes from appended claims that do not specify a particular complex formation process. Rather, additional processing steps may, for example, be employed to eliminate free perfume associated with extruded complexes prior to their inclusion into a composition.

The analytical method for determining the percent of perfume complexed, as shown in Table II, determines the free perfume level in the complex by dissolving a sample in tetrahydrofuran (THF) adding an internal standard, and analyzing by capillary gas chromatography (GC). The complexed perfume level is measured by extracting the same sample in acetone containing an internal standard, and analyzing by GC.

Complexation Efficiency=% Complexed/[% Complexed+% Free]

Perfume Compositions

A perfume composition comprises perfume raw materials. At least a portion of the perfume raw materials may have a complex stability constant of about 3.0 or less; about 2.5 or less, about 2.0 or less, about 1.0 or less, to about 0, to about −1, to about −2, or any combination thereof. Some of the perfume raw material may have a c Log P of about 2.5 or less, about 2.0 or less, about 1.5 or less, about 1.0 or less, to about −3. Some of the perfume raw materials may have a weight average molecular weight of about 200 Daltons or less, about 180 Daltons or less, about 150 Daltons or less, about 100 Daltons or less, to about 50 Daltons. A perfume raw material will have an odor detection threshold. At least a portion of the perfume raw materials in a perfume composition will have an odor detection threshold of about 7-log molar concentration or greater; about 8-log molar concentration or greater; about 9-log molar concentration or greater; to about 11.5-log molar concentration.

The perfume composition comprises about 10% or more, by weight of the perfume, of perfume raw materials which have a complex stability constant of about 3.0 or less, a c Log P of about 2.5 or less, and a weight average molecular weight of about 200 Daltons or less. Going further, the perfume composition may comprise about 20% or more; about 30% or more; about 40% or more, or about 50% or more, up to 100%; of perfume raw materials which have a complex stability constant of about 3.0 or less, a c Log P of about 2.5 or less, and a weight average molecular weight of about 200 Daltons or less. In addition, a perfume composition may also include perfume raw materials with an odor detection threshold of about 7-log molar concentration.

A representative, non-limiting, list of perfume raw materials that have a complex stability constant of about 3.0 or less, a c Log P of about 2.5 or less, and a weight average molecular weight of about 200 Daltons or less is included in the chart below.

| CAS Number | Name | LogP (v3.0) | Formula Weight | Odor Detection Threshold, Neural Net model | bCD Complex Stability Constant |
|---|---|---|---|---|---|
| 10031-96-6 | eugenyl formate | 2.35 | 192.21 | 8.84 | 2.71 |
| 100-52-7 | Benzaldehyde | 1.4 | 106.12 | 7.45 | 2.19 |
| 10094-40-3 | 2-hexen-1-yl acetate | 2.21 | 142.20 | 8.20 | 1.45 |
| 101-39-3 | alpha-methyl cinnamaldehyde | 2.18 | 146.19 | 8.83 | 1.08 |
| 101-41-7 | Methyl phenylacetate | 1.89 | 150.18 | 8.02 | 2.14 |
| 101-48-4 | Viridine (PADMA) | 1.65 | 166.22 | 8.01 | 2.26 |
| 101-97-3 | Ethyl 2-phenylacetate | 2.39 | 164.20 | 8.63 | 2.25 |
| 103-25-3 | methyl hydrocinnamate | 2.04 | 164.20 | 8.20 | 2.24 |
| 103-26-4 | Methyl cinnamate | 2.44 | 162.19 | 8.97 | 2.07 |
| 103-45-7 | 2-Phenylethyl acetate | 2.07 | 164.20 | 8.15 | 1.54 |
| 103-54-8 | Cinnamyl acetate | 2.49 | 176.22 | 8.51 | 1.53 |
| 104-09-6 | lilac acetaldehyde | 2.12 | 134.18 | 9.36 | 2.67 |
| 104-20-1 | 4-(p-Methoxyphenyl)-2-butanone (frambinone) | 1.88 | 178.23 | 8.86 | 1.72 |
| 104-46-1 | Anethole | 2.43 | 148.20 | 8.79 | 2.34 |
| 104-50-7 | gamma-Octalactone | 2.06 | 142.20 | 8.30 | 2.94 |
| 104-53-0 | 3-phenyl propionaldehyde | 1.65 | 134.18 | 8.95 | 2.47 |
| 104-54-1 | Cinnamic alcohol | 1.68 | 134.18 | 8.58 | 2.15 |
| 104-55-2 | Cinnamic aldehyde | 1.92 | 132.16 | 8.56 | 2.37 |
| 104-62-1 | Phenethyl formate | 1.82 | 150.18 | 8.10 | 2.32 |
| 104-64-3 | 3-phenyl propyl formate | 2.22 | 164.20 | 8.51 | 2.46 |
| 105-01-1 | Isobutyl furylpropionate | 2.34 | 196.25 | 8.60 | 2.30 |
| 10521-96-7 | Styryl acetate | 2.3 | 162.19 | 8.60 | 1.47 |
| 105-86-2 | geranyl formate | 2.44 | 182.26 | 8.49 | −1.85 |
| 10606-47-0 | 3-Hepten-1-ol | 1.79 | 114.19 | 8.47 | 2.11 |
| 106-22-9 | Citronellol | 2.49 | 156.27 | 8.37 | −0.64 |
| 106-24-1 | trans-Geraniol | 1.95 | 154.25 | 9.36 | −2.13 |
| 106-25-2 | Nerol | 1.95 | 154.25 | 9.36 | −2.13 |
| 106-26-3 | Neral | 2.33 | 152.24 | 8.48 | −1.82 |
| 106-72-9 | melon heptenal (melonal) | 2.09 | 140.23 | 8.09 | −0.64 |
| 107-03-9 | Propyl mercaptan | 1.87 | 76.16 | 9.04 | 0.65 |
| 1073-26-3 | 2-Propionylpyrrole | 1.37 | 123.15 | 8.13 | 1.88 |
| 110458-85-0 | 5,6-Dimethyl-1-(1-methylethenyl)bicyclo[2.2.1]hept-5-ene-2-methanol | 2.36 | 192.30 | 9.46 | 1.27 |
| 1123-85-9 | Hydratopic alcohol | 1.85 | 136.19 | 8.19 | 1.99 |
| 1131-62-0 | 3,4-Dimethoxyacetophenone | 1.7 | 180.20 | 8.15 | 1.63 |
| 116-26-7 | Safranal | 2.4 | 150.22 | 8.54 | 1.30 |
| 118-93-4 | 2-Hydroxyacetophenone | 1.97 | 136.15 | 8.15 | 1.38 |
| 1197-06-4 | cis-carveol | 1.86 | 152.24 | 8.60 | 0.32 |
| 1205-17-0 | ocean propanal (helional) | 1.77 | 192.21 | 8.89 | 2.67 |
| 120-58-1 | Isosafrol | 2.01 | 162.19 | 8.45 | 2.52 |
| 120-72-9 | Indole | 2.34 | 117.15 | 8.20 | 2.19 |
| 120-75-2 | 2-Methylbenzothiazole | 2.14 | 149.21 | 8.12 | 2.83 |
| 121-32-4 | Ethyl vanillin | 1.53 | 166.18 | 10.32 | 2.41 |
| 121-33-5 | Vanillin | 1.04 | 152.15 | 9.93 | 2.36 |
| 121-98-2 | Methyl p-anisate | 1.99 | 166.18 | 8.54 | 2.05 |
| 122-63-4 | Benzyl propionate | 2.24 | 164.20 | 8.29 | 2.01 |
| 122-72-5 | 3-phenyl propyl acetate | 2.48 | 178.23 | 8.70 | 1.73 |
| 122-78-1 | phenyl acetaldehyde | 1.46 | 120.15 | 8.40 | 2.30 |
| 123-08-0 | p-Hydroxybenzaldehyde | 1.29 | 122.12 | 9.34 | 2.28 |
| 123-11-5 | para-anisaldehyde | 1.53 | 136.15 | 7.72 | 2.29 |
| 123-92-2 | Isoamyl acetate | 1.87 | 130.19 | 7.12 | 1.33 |
| 13327-56-5 | Ethyl 3-methylthiopropionate | 1.47 | 148.22 | 8.09 | 1.88 |
| 134-20-3 | Methyl anthranilate | 1.58 | 151.17 | 8.22 | 1.69 |
| 13494-08-1 | 1,2-Cyclopentanedione, 3-ethyl- | 0.5 | 126.16 | 8.29 | 2.72 |
| 134-96-3 | Syringaldehyde | 0.94 | 182.18 | 9.89 | 2.48 |
| 13678-68-7 | furfuryl thioacetate | 1.09 | 156.20 | 8.11 | 1.33 |
| 13679-85-1 | blackberry thiophenone | 0.73 | 156.18 | 8.44 | 2.06 |
| 140-39-6 | p-Cresyl acetate | 2.17 | 150.18 | 8.10 | 1.67 |
| 14049-11-7 | linalool oxide (pyranoid) | 1.89 | 170.25 | 8.45 | 2.62 |
| 141-27-5 | Geranial | 2.33 | 152.24 | 8.48 | −1.82 |
| 142653-61-0 | Parmanyl | 1.75 | 153.22 | 8.13 | 2.05 |
| 142-83-6 | Sorbinaldehyde | 1.29 | 96.13 | 8.57 | 2.29 |
| 14360-50-0 | Pentyl 2-furyl ketone | 2.49 | 166.22 | 9.39 | 2.44 |
| 150-19-6 | m-Guaiacol | 1.39 | 124.14 | 8.16 | 2.02 |
| 1504-55-8 | alpha-Methylcinnamic alcohol (cypriol) | 1.73 | 148.20 | 8.68 | 0.74 |
| 15111-56-5 | Ethyl cyclohex-3-enecarboxylate | 1.86 | 154.21 | 8.47 | 2.78 |
| 1516-17-2 | 2,4-Hexadienyl acetate | 1.75 | 110.16 | 8.30 | 1.36 |
| 15174-69-3 | 4-Hydroxy-3-methylbenzaldehyde | 1.63 | 136.15 | 10.25 | 2.24 |
| 15186-51-3 | Furan, 3-methyl-2-(3-methyl-2-butenyl)- | 2.04 | 150.22 | 8.26 | −0.46 |
| 1540-28-9 | n-Pentyl acetoacetate | 1.63 | 172.22 | 8.04 | 1.79 |
| 1552-67-6 | Ethyl 2-hexenoate | 2.49 | 142.20 | 8.30 | 2.12 |

-continued

| CAS Number | Name | LogP (v3.0) | Formula Weight | Odor Detection Threshold, Neural Net model | bCD Complex Stability Constant |
|---|---|---|---|---|---|
| 15679-12-6 | 2-Ethyl-4-methylthiazole | 1.69 | 127.20 | 8.31 | 2.13 |
| 15679-13-7 | tropical thiazole | 2.12 | 141.23 | 8.25 | 2.33 |
| 16251-77-7 | Trifernal | 2.28 | 148.20 | 8.87 | 2.51 |
| 1646-26-0 | Coumarone | 1.9 | 160.17 | 8.64 | 1.90 |
| 16491-25-1 | 2,4-Hexadienyl propionate | 2.44 | 154.21 | 8.72 | 1.97 |
| 1679-07-8 | Cyclopentyl mercaptan | 2.24 | 102.19 | 9.09 | 1.47 |
| 1679-09-0 | 2-Methyl-2-butanethiol | 2.45 | 104.21 | 9.16 | 0.79 |
| 16957-70-3 | trans-2-Methyl-2-pentenoic acid (Strawberriff) | 1.33 | 114.14 | 8.78 | 0.65 |
| 1708-34-5 | 2-Hexyl-1,3-dioxolane | 2.17 | 158.24 | 8.11 | 2.56 |
| 1708-81-2 | cis-3-Hepten-1-ol | 1.79 | 114.19 | 8.47 | 2.11 |
| 1708-82-3 | 3-Hexenyl acetate | 2.18 | 142.20 | 8.16 | 1.48 |
| 17102-64-6 | Trans,trans-2,4-Hexadien-1-01 | 0.96 | 98.14 | 8.22 | 2.06 |
| 1754-62-7 | Methyl Trans-Cinnamate, 99% | 2.44 | 162.19 | 8.97 | 2.07 |
| 1759-28-0 | 4-Methyl-5-vinylthiazole | 1.51 | 125.19 | 8.56 | 1.62 |
| 17626-75-4 | 2-Propylthiazole | 1.51 | 127.20 | 8.23 | 1.79 |
| 18031-40-8 | (S),(−)-Perillaaldehyde | 2.34 | 150.22 | 9.80 | 1.85 |
| 18277-27-5 | 2-(1-Methylpropyl)thiazole | 1.9 | 141.23 | 8.25 | 1.71 |
| 18479-68-0 | (+)-P-Menth-1-en-9-ol, 97%, mixture of isomers | 2.26 | 154.25 | 8.87 | 1.66 |
| 18640-74-9 | Isobutyl thiazole | 1.92 | 141.23 | 8.29 | 2.02 |
| 18829-55-5 | trans-2-Heptenal | 2.1 | 112.17 | 8.76 | 2.33 |
| 18881-04-4 | (1S)-(−)-cis-Verbenol | 2.03 | 152.24 | 8.09 | 2.61 |
| 189440-77-5 | Anapear | 2.3 | 154.21 | 8.78 | 2.20 |
| 1901-38-8 | alpha-Campholenic alcohol | 2.03 | 154.25 | 8.08 | 1.32 |
| 19788-49-9 | Ethyl 2-mercaptopropionate | 1.41 | 134.19 | 8.39 | 0.99 |
| 19819-98-8 | 2-Methylphenethyl alcohol | 1.66 | 136.19 | 8.46 | 2.36 |
| 2046-17-5 | Methyl 4-phenylbutyrate | 2.46 | 178.23 | 8.75 | 2.37 |
| 20474-93-5 | Allyl crotonate | 1.63 | 126.16 | 8.29 | 2.24 |
| 2051-78-7 | Allyl butyrate | 1.88 | 128.17 | 8.17 | 2.21 |
| 2051-96-9 | Benzyl lactate | 1.35 | 180.20 | 8.15 | 1.70 |
| 20665-85-4 | Vanillin isobutyrate | 1.92 | 222.24 | 8.20 | 2.20 |
| 2111-75-3 | perillaldehyde | 2.34 | 150.22 | 9.80 | 1.85 |
| 2142-94-1 | Neryl Formate | 2.44 | 182.26 | 8.49 | −1.85 |
| 2179-58-0 | Allyl methyl disulfide | 1.9 | 120.23 | 8.59 | 1.44 |
| 2179-60-4 | Methyl propyl disulfide | 2.28 | 122.24 | 8.56 | 1.97 |
| 21835-00-7 | 2-Cyclopenten-1-one, 2-hydroxy-3,4-dimethyl- | −0.02 | 126.16 | 8.91 | 0.76 |
| 21835-01-8 | 3-Ethyl-2-hydroxy-2-cyclopenten-1-one | 0.06 | 126.16 | 8.79 | 2.41 |
| 22104-78-5 | 2-Octenol-1 | 2.27 | 128.21 | 8.81 | 2.24 |
| 2217-33-6 | Tetrahydrofurfuryl butyrate | 1.54 | 172.22 | 8.40 | 2.22 |
| 22451-63-4 | Allo-ocimenol | 2.42 | 152.24 | 8.51 | −0.99 |
| 22460-95-3 | 7-Octene-1,6-diol, 3,7-dimethyl- | 1.33 | 172.27 | 8.27 | 0.79 |
| 22924-15-8 | 3-Ethoxybenzaldehyde | 1.99 | 150.18 | 8.14 | 2.33 |
| 22927-13-5 | 2-Ethylbenzaldehyde | 2.06 | 134.18 | 8.78 | 2.53 |
| 2305-21-7 | 2-hexen-1-ol | 1.3 | 100.16 | 8.09 | 2.06 |
| 23495-12-7 | Phenoxyethyl propionate | 2.43 | 194.23 | 8.92 | 1.78 |
| 23911-56-0 | Nerolione | 2.02 | 174.20 | 8.74 | 2.04 |
| 2445-83-2 | 7-Methylcoumarin | 2.42 | 160.17 | 8.79 | 2.78 |
| 2463-63-0 | Butylacrolein | 2.1 | 112.17 | 8.76 | 2.33 |
| 2497-18-9 | 2-Hexen-1-yl acetate | 2.21 | 142.20 | 8.20 | 1.45 |
| 2555-49-9 | Ethyl phenoxyacetate | 2.04 | 180.20 | 8.36 | 1.93 |
| 26553-46-8 | Ethyl trans-3-hexenoate | 2.25 | 142.20 | 8.34 | 2.14 |
| 8/6/2719 | N-Acetyl methyl anthranilate | 1.21 | 193.20 | 8.00 | 1.48 |
| 27829-72-7 | Ethyl trans-2-hexenoate | 2.49 | 142.20 | 8.30 | 2.12 |
| 27939-60-2 | Vertoliff (triplal extra) | 1.8 | 138.21 | 9.24 | 1.71 |
| 28069-72-9 | (2E,6Z)-Nona-2,6-dien-1-ol | 2.43 | 140.23 | 9.59 | 2.24 |
| 28977-58-4 | Ocimenol | 2.02 | 152.24 | 8.71 | −0.59 |
| 29414-56-0 | 2,6-Dimethyl-1,5,7-octatrienol-3 | 1.96 | 152.24 | 8.89 | −0.76 |
| 29548-14-9 | p-Menth-1-ene-9-al | 2.24 | 152.24 | 9.40 | 1.85 |
| 30361-28-5 | 2,4-Octadien-1-al | 2.45 | 124.18 | 9.33 | 2.32 |
| 30954-98-4 | Propyl anthranilate | 2.47 | 179.22 | 8.88 | 1.87 |
| 3194-17-0 | 2-Pentanoylfuran | 1.99 | 152.19 | 8.97 | 2.40 |
| 32272-48-3 | 4-Ethyl-2-methylthiazole | 1.7 | 127.20 | 8.32 | 2.25 |
| 32764-98-0 | Jasmolactone | 2.36 | 168.24 | 8.72 | 2.96 |
| 33467-73-1 | cis-3-Hexenyl formate | 1.69 | 128.17 | 8.22 | 2.25 |
| 3391-86-4 | 1-Octenol-3 | 2.36 | 128.21 | 8.29 | 2.19 |
| 3581-91-7 | 4,5-Dimethylthiazole | 0.91 | 113.18 | 8.10 | 1.30 |
| 3583-00-4 | 4,4-Dimethyl-5-isopropyl-1,3-dioxolane | 1.92 | 158.24 | 8.99 | 1.98 |
| 35926-04-6 | 1-Hexen-3-yl acetate | 2.31 | 142.20 | 8.02 | 1.68 |
| 36701-01-6 | Furfuryl valerate | 1.89 | 182.22 | 8.39 | 2.12 |

-continued

| CAS Number | Name | LogP (v3.0) | Formula Weight | Odor Detection Threshold, Neural Net model | bCD Complex Stability Constant |
|---|---|---|---|---|---|
| 36806-46-9 | 2,6-Dimethyl-6-hepten-1-ol | 2.4 | 142.24 | 8.07 | 0.76 |
| 3681-71-8 | cis-3-Hexenyl acetate | 2.18 | 142.20 | 8.16 | 1.48 |
| 3681-82-1 | trans-3-Hexenyl acetate | 2.18 | 142.20 | 8.16 | 1.48 |
| 36880-33-8 | 5-Ethyl-2-thiophenecarbaldehyde | 1.85 | 140.20 | 8.19 | 2.64 |
| 37973-51-6 | 2-Phenyl-1(2)propenyl-1 ester | 2.47 | 176.22 | 8.82 | 0.44 |
| 38142-45-9 | 3-Cyclohexene-1-ethanol, 4-methyl-.beta.-methylene-, (R)- | 1.84 | 152.24 | 8.62 | 1.58 |
| 39252-02-3 | Furfuryl hexanoate | 2.38 | 196.25 | 8.80 | 2.17 |
| 39677-52-6 | 3-Methoxy Cinnamaldehyde | 1.86 | 162.19 | 8.84 | 2.49 |
| 40010-99-9 | 3-Acetyl-5-butyldihydro-2(3H)-furanone | 1.71 | 184.24 | 8.57 | 2.58 |
| 40790-29-2 | Pyrazine, 3-butyl-2,5-dimethyl- | 2.29 | 164.25 | 8.18 | 2.48 |
| 409-02-9 | Methyl Heptenone | 2.27 | 126.20 | 8.58 | 2.38 |
| 4175-66-0 | 2,5-Dimethylthiazole | 0.94 | 113.18 | 8.08 | 1.63 |
| 4180-23-8 | (E)-anethol | 2.43 | 148.20 | 8.79 | 2.34 |
| 41847-88-5 | Phenylethyl oxy-acetaldehyde | 1.55 | 164.20 | 8.61 | 2.34 |
| 42348-12-9 | 3-Ethyl-2-hydroxy-4-methylcyclopent-2-en-1-one | 0.54 | 140.18 | 9.10 | 2.58 |
| 3/5/4313 | (E,E)-2,4-heptadien-1-al | 1.98 | 110.16 | 9.00 | 2.29 |
| 6/1/4364 | Cinnamic aldehyde dimethyl acetal | 2.02 | 178.23 | 8.44 | 2.03 |
| 4501-58-0 | Campholene aldehyde | 2.2 | 152.24 | 8.31 | 1.43 |
| 4634-89-3 | cis-4-Hexenal | 1.05 | 98.14 | 9.24 | 2.26 |
| 4643-25-8 | 2-Hepten-4-one | 1.85 | 112.17 | 8.31 | 2.21 |
| 4643-27-0 | 2-Octen-4-one | 2.42 | 126.20 | 8.70 | 2.43 |
| 473-67-6 | Verbenol | 2.03 | 152.24 | 8.09 | 2.61 |
| 4748-78-1 | 4-Ethylbenzaldehyde | 2.39 | 134.18 | 9.19 | 2.54 |
| 491-04-3 | Piperitol | 2.4 | 154.25 | 8.70 | 1.72 |
| 491-09-8 | piperitenone | 2.33 | 150.22 | 8.40 | −1.20 |
| 491-31-6 | Isocoumarin | 1.69 | 146.15 | 8.63 | 2.45 |
| 491-35-0 | Lepidine | 2.46 | 143.19 | 8.13 | 2.44 |
| 11/8/4940 | ethyl maltol | 0.17 | 140.14 | 7.44 | 1.94 |
| 496-77-5 | Butyroin | 1.29 | 144.21 | 8.36 | 2.22 |
| 499-44-5 | Hinokitiol | 1.35 | 164.20 | 9.32 | 2.71 |
| 50888-63-6 | Pyrazine, 2-butyl-3,5-dimethyl- | 2.3 | 164.25 | 8.19 | 2.27 |
| 53046-97-2 | cis-3, cis-6-nonadienol | 2.45 | 140.23 | 9.52 | 2.16 |
| 53398-78-0 | trans-2-Hexenyl formate | 1.71 | 128.17 | 8.31 | 2.23 |
| 53399-81-8 | Ethyl 2-methyl-4-pentenoate | 2.26 | 142.20 | 8.16 | 2.08 |
| 536-50-5 | 1-(4-Methylphenyl)ethanol | 2 | 136.19 | 8.07 | 2.39 |
| 536-59-4 | Perillyl alcohol | 1.83 | 152.24 | 8.58 | 1.69 |
| 536-60-7 | Cumic alcohol | 2.39 | 150.22 | 8.68 | 2.39 |
| 5392-40-5 | Citral | 2.33 | 152.24 | 8.48 | −1.82 |
| 5396-89-4 | Benzyl acetoacetate | 1.43 | 192.21 | 8.05 | 1.45 |
| 12/2/5406 | p-Methylhydrocinnamic aldehyde | 2.19 | 148.20 | 9.57 | 2.84 |
| 541-58-2 | 2,4-Dimethylthiazole | 1.24 | 113.18 | 8.08 | 1.89 |
| 5426-78-8 | Acetaldehyde phenyl ethyl acetal | 2.22 | 166.22 | 8.56 | 1.83 |
| 6/6/5462 | Canthoxal | 2.16 | 178.23 | 8.80 | 2.49 |
| 6/8/5466 | Ethyl 3-mercaptopropionate | 1.36 | 134.19 | 8.92 | 1.25 |
| 5471-51-2 | Raspberry ketone | 1.58 | 164.20 | 7.67 | 1.70 |
| 554-14-3 | 2-Methylthiophene | 2.06 | 98.16 | 8.11 | 1.52 |
| 55722-59-3 | 3,6-Octadienal, 3,7-dimethyl- | 2.34 | 152.24 | 8.51 | −1.89 |
| 5577-44-6 | 2,4-Octadienal | 2.45 | 124.18 | 9.33 | 2.32 |
| 5660-60-6 | Cinnamaldehyde ethylene glycol acetal | 2.15 | 176.22 | 8.04 | 2.16 |
| 56805-23-3 | trans-3, cis-6-nonadienol | 2.45 | 140.23 | 9.52 | 2.16 |
| 57266-86-1 | 2-Heptenal, (2Z)- | 2.1 | 112.17 | 8.76 | 2.33 |
| 57500-00-2 | Methyl furfuryl disulfide | 1.92 | 160.25 | 8.19 | 2.38 |
| 579-74-8 | o-Acetylanisole | 1.55 | 150.18 | 8.40 | 1.56 |
| 58461-27-1 | Lavandulol | 1.95 | 154.25 | 8.98 | −1.82 |
| 585-74-0 | 3-Methylacetophenone | 2.27 | 134.18 | 8.23 | 1.65 |
| 589-18-4 | p-Tolyl alcohol | 1.62 | 122.17 | 8.01 | 2.35 |
| 59020-85-8 | Furfuryl thiopropionate | 1.61 | 170.23 | 8.45 | 2.16 |
| 59021-02-2 | 2-Mercaptomethylpyrazine | 0.34 | 126.18 | 8.26 | 0.66 |
| 5910-85-0 | 2,4-Heptadienal | 1.98 | 110.16 | 9.00 | 2.29 |
| 5912-86-7 | cis-iso-Eugenol | 1.85 | 164.20 | 8.60 | 2.38 |
| 5925-68-8 | S-Ethyl benzothioate | 2.21 | 152.21 | 8.74 | 1.83 |
| 5932-68-3 | trans-Isoeugenol | 1.85 | 164.20 | 8.60 | 2.38 |
| 606-27-9 | Methyl 2-nitrobenzoate | 1.57 | 181.15 | 8.45 | 2.25 |
| 606-45-1 | Methyl o-methoxybenzoate | 1.79 | 166.18 | 8.56 | 2.15 |
| 613-70-7 | Guaiacyl acetate | 1.55 | 166.18 | 8.18 | 1.57 |
| 616-44-4 | 3-Methylthiophene | 2.23 | 98.16 | 8.51 | 1.52 |
| 6191-71-5 | cis-4-Hepten-1-ol | 1.77 | 114.19 | 8.46 | 2.11 |
| 6192-44-5 | beta-Phenoxy ethyl acetate | 1.87 | 180.20 | 8.51 | 1.26 |
| 61931-81-5 | cis-3-Hexenyl lactate | 1.34 | 172.22 | 8.20 | 1.76 |

| CAS Number | Name | LogP (v3.0) | Formula Weight | Odor Detection Threshold, Neural Net model | bCD Complex Stability Constant |
|---|---|---|---|---|---|
| 620-23-5 | meta-tolyl aldehyde | 2.13 | 120.15 | 8.79 | 2.38 |
| 623-15-4 | 4-(2-Furyl)-3-buten-2-one | 1.7 | 136.15 | 8.42 | 1.38 |
| 624-92-0 | Dimethyl disulfide | 1.06 | 94.19 | 8.64 | 0.27 |
| 6290-14-8 | Cyclopentyl isobutyrate | 2.29 | 156.22 | 8.42 | 2.08 |
| 6314-97-2 | Phenylacetaldehyde diethyl acetal | 2.29 | 194.27 | 9.02 | 2.37 |
| 637-65-0 | tetrahydrofurfuryl propionate | 0.93 | 158.20 | 8.02 | 2.07 |
| 638-02-8 | 2,5-Dimethylthiophene | 2.36 | 112.19 | 8.64 | 2.04 |
| 64988-06-3 | Ethyl 2-methoxybenzyl ether | 1.98 | 166.22 | 8.23 | 2.27 |
| 65405-67-6 | p-Methoxy-alpha-methyl cinnamaldehyde | 2 | 176.22 | 8.85 | 1.16 |
| 65405-73-4 | Geranyl oxyacetaldehyde | 2.32 | 196.29 | 8.71 | −1.88 |
| 67028-40-4 | Ethyl (p-tolyloxy)acetate | 2.49 | 194.23 | 8.45 | 2.18 |
| 6728-26-3 | Trans-2-Hexenal | 1.57 | 98.14 | 8.41 | 2.26 |
| 6728-31-0 | cis-4-Heptenal | 1.85 | 112.17 | 9.51 | 2.33 |
| 67633-97-0 | 3-Mercapto-2-pentanone | 1.37 | 118.19 | 8.86 | 0.23 |
| 67634-07-5 | 3,5,6-Trimethyl-3-cyclohexene-1-carbaldehyde | 2.37 | 152.24 | 8.63 | 1.97 |
| 67634-16-6 | Floralol | 1.83 | 140.23 | 8.38 | 1.50 |
| 67634-17-7 | 2,4-Dimethyl-3-cyclohexene-1-methanol | 1.81 | 140.23 | 8.51 | 1.61 |
| 67746-30-9 | trans-2-Hexenal diethyl acetal | 2.34 | 172.27 | 8.19 | 2.13 |
| 67801-65-4 | 3,6-ivy carbaldehyde | 1.8 | 138.21 | 9.25 | 2.09 |
| 67845-46-9 | p-Methyl phenoxy acetaldehyde | 1.76 | 150.18 | 8.64 | 2.40 |
| 6789-80-6 | (Z)-3-hexen-1-al | 1.43 | 98.14 | 8.97 | 2.26 |
| 68039-48-5 | Dimethyl cyclohexene carboxaldehyde | 1.82 | 138.21 | 9.18 | 1.65 |
| 68039-49-6 | 2,4-Dimethyl-3-Cyclohexene-1-carboxaldehyde (Ligustral) | 1.78 | 138.21 | 9.24 | 1.76 |
| 68133-76-6 | cis-3-Hexenyl pyruvate | 1.9 | 170.21 | 8.50 | 1.30 |
| 68737-61-1 | 3,5-ivy carbaldehyde | 1.82 | 138.21 | 9.18 | 1.65 |
| 698-76-0 | delta-Octalactone | 2.03 | 142.20 | 8.24 | 2.83 |
| 699-10-5 | Methyl benzyl disulfide | 2.47 | 170.29 | 8.45 | 2.96 |
| 701-70-2 | 1-Phenylbutan-2-ol | 2.21 | 150.22 | 8.59 | 2.26 |
| 7452-79-1 | Ethyl 2-methylbutyrate | 1.91 | 130.19 | 7.27 | 1.75 |
| 74-93-1 | Methyl mercaptan | 0.58 | 48.10 | 8.63 | 0.43 |
| 7493-63-2 | Allyl anthranilate | 2.31 | 177.20 | 8.48 | 1.95 |
| 7493-71-2 | Allyl tiglate | 1.86 | 140.18 | 8.12 | 0.69 |
| 75-08-1 | Ethanethiol | 1.37 | 62.13 | 8.87 | 0.63 |
| 75-18-3 | dimethyl sulfide | 1.24 | 62.13 | 8.33 | 0.86 |
| 75-33-2 | 2-Propanethiol | 1.65 | 76.16 | 9.26 | 0.87 |
| 7540-51-4 | (−)-Citronellol | 2.49 | 156.27 | 8.37 | 0.64 |
| 7549-33-9 | Anisyl propionate | 2.23 | 194.23 | 8.45 | 2.08 |
| 75-66-1 | tert-Butyl mercaptan | 1.65 | 90.18 | 9.13 | 1.13 |
| 764-40-9 | 2,4-Pentadienal | 0.7 | 82.10 | 8.16 | 2.37 |
| 76649-25-7 | 3,6-Nonadien-1-ol | 2.45 | 140.23 | 9.52 | 2.16 |
| 774-48-1 | Benzaldehyde diethyl acetal | 2.03 | 180.25 | 8.57 | 2.35 |
| 7774-74-5 | 2-Thienyl mercaptan | 1.77 | 116.20 | 8.00 | 0.81 |
| 7774-79-0 | 4-(p-Tolyl)-2-butanone | 2.46 | 162.23 | 8.64 | 2.01 |
| 7774-96-1 | Isoeugenyl formate | 2.35 | 192.21 | 8.84 | 2.71 |
| 7786-44-9 | 2,6-Nonadien-1-ol | 2.43 | 140.23 | 9.59 | 2.24 |
| 7786-61-0 | 2-Methoxy-4-vinylphenol | 2.24 | 150.18 | 8.71 | 2.37 |
| 7786-67-6 | p-Menth-8-en-3-ol (8CI) | 2.48 | 154.25 | 8.42 | 2.29 |
| 81925-81-7 | filbert heptenone (Filbertone) | 2.31 | 126.20 | 8.06 | 1.92 |
| 84434-18-4 | Gardamide | 2.16 | 191.27 | 8.08 | 1.98 |
| 85-91-6 | Dimethyl anthranilate | 2.19 | 165.19 | 8.13 | 2.08 |
| 870-23-5 | Allyl mercaptan | 1.42 | 74.14 | 9.00 | 0.85 |
| 87-25-2 | Ethyl anthranilate | 2.05 | 165.19 | 8.58 | 1.84 |
| 874-66-8 | cinnamon acrolein | 1.29 | 136.15 | 8.09 | 0.92 |
| 881-68-5 | Vanillin acetate | 0.95 | 194.19 | 8.11 | 1.94 |
| 89-79-2 | Isopulegol | 2.48 | 154.25 | 8.42 | 2.29 |
| 90-02-8 | Salicylaldehyde | 1.4 | 122.12 | 8.95 | 2.21 |
| 90-05-1 | Guaiacol | 1.33 | 124.14 | 8.06 | 1.98 |
| 90-87-9 | Hydratropaldehyde dimethyl acetal | 2.12 | 180.25 | 8.60 | 2.24 |
| 91-64-5 | Coumarin | 1.68 | 146.15 | 8.55 | 2.47 |
| 928-94-9 | (Z)-2-hexen-1-ol | 1.3 | 100.16 | 8.09 | 2.06 |
| 928-95-0 | (E)-2-hexen-1-ol | 1.3 | 100.16 | 8.09 | 2.06 |
| 928-96-1 | cis-3-Hexen-1-ol | 1.3 | 100.16 | 8.06 | 2.06 |
| 93-16-3 | Methyl isoeugenol | 2.05 | 178.23 | 8.70 | 2.49 |
| 93-29-8 | Isoeugenyl acetate | 2.17 | 206.24 | 8.38 | 1.94 |
| 93-53-8 | 2-phenyl propionaldehyde | 2.06 | 134.18 | 8.43 | 2.21 |
| 93-54-9 | 1-Phenyl-1-propanol | 1.77 | 136.19 | 8.21 | 2.03 |
| 93-58-3 | Methyl benzoate | 1.86 | 136.15 | 8.03 | 2.00 |
| 93-89-0 | Ethyl benzoate | 2.25 | 150.18 | 8.60 | 2.18 |

-continued

| CAS Number | Name | LogP (v3.0) | Formula Weight | Odor Detection Threshold, Neural Net model | bCD Complex Stability Constant |
|---|---|---|---|---|---|
| 93893-89-1 | Citronitrile | 2.34 | 171.24 | 8.57 | 1.27 |
| 93-92-5 | Styrallyl acetate | 2.2 | 164.20 | 8.18 | 1.54 |
| 94089-01-7 | Butanoic acid, 2-methyl-, 2-hexenyl ester, (E)- | 1.6 | 134.24 | 9.32 | 1.41 |
| 94-86-0 | Vanitrope | 2.42 | 178.23 | 8.53 | 2.39 |
| 95-20-5 | 2-Methylindole | 2.43 | 131.18 | 8.53 | 2.58 |
| 97-53-0 | Eugenol | 2.21 | 164.20 | 8.57 | 2.51 |

One grouping of perfume raw materials that have a complex stability constant of about 3.0 or less, a c Log P of about 2.5 or less, and a weight average molecular weight of about 200 Daltons or less includes beta gamma hexanol; cis 3 hexenyl acetate; ethyl-2-methyl butyrate; amyl-acetate (isomer blends); vanillin; anethole; methyl isoeugenol; guiacol; floralol; ethyl vanillin; 2,6-nonadien-1-ol; coumarin; and combinations thereof.

Another group of perfume raw materials that have a complex stability constant of about 3.0 or less, a C log P of about 2.5 or less, and a weight average molecular weight of about 200 Daltons or less includes ethyl-2-methyl butyrate; beta gamma hexanol; iso amyl acetate; amyl acetate; cis-3-Hexenyl acetate; gamma-Octalactone; ethyl vanillin; vanillin; benzaldehyde; and combinations thereof.

An additional group of perfume raw materials that have a complex stability constant of about 3.0 or less, a C log P of about 2.5 or less, and a weight average molecular weight of about 200 Daltons or less includes dimethyl anthranilate; iso-eugenyl acetate; canthoxal; 3,6-nonadien-1-ol, triplal; and combinations thereof.

Surfactant

The compositions can include a surfactant. A surfactant is generally present at a level of about 0.05% to about 5%, by weight of the composition, but can contain, from about 0.5% to about 5.0%; from about 1.0% to about 4%; from about 1.5% to about 3.5%; from about 1.75% to about 2.5%; about 2%, or any combination thereof. The surfactant can have a HLB range of about 2 to about 14; about 6 to about 12; about 8 to about 10; or any combination thereof. The surfactant can be free of polyoxyethylene sorbitan fatty acids. The surfactant can comprise, for example, a $C_{20-40}$ Pareth-10. Another suitable surfactant is a nonionic exthoxylated linear alcohol with a carbon chain length of 20-40. Suitable surfactants include PERFORMATHOX™ 450 ethoxylate.

Free Perfume

In addition to any perfume that comes in as part of a cyclodextrin perfume complex, a composition may comprise free perfume. Free perfume is perfume that is added to the composition that is not part of a cyclodextrin perfume complex. Free perfume can be added to the composition in order to give an initial perfume. It can be the same or different than the perfume included in the cyclodextrin perfume complex. Free perfume may be added to a personal aerosol composition at a level of about 0.1% to about 20%, at a level of about 5% to about 15%, or any combination thereof, by weight of the composition.

Other Materials

The compositions can also include other materials known for use in antiperspirant, deodorant or other personal care products, including those materials that are known to be suitable for topical application to skin. Non-limiting examples include dyes or colorants, emulsifiers, distributing agents, pharmaceuticals or other topical actives, skin conditioning agents or actives, deodorant agents, antimicrobials, preservatives, surfactants, processing aides such as viscosity modifiers and wash-off aids.

Examples/Combinations

A. An anhydrous stick composition, comprising a deodorant active, an antiperspirant active, or a combination thereof a carrier; a structurant; and a cyclodextrin perfume complex, wherein the cyclodextrin perfume complex comprises a cyclodextrin and a perfume comprising perfume raw materials and wherein 10% or more, by weight of the perfume, of the perfume raw materials have: a cyclodextrin complex stability constant of about 3.0 or less, a C log P of about 2.5 or less; and a weight average molecular weight of about 200 Daltons or less.

B. The anhydrous stick composition of paragraph A, wherein the cyclodextrin complex stability constant (log k) is from about −2.0 to about 2.5.

C. The anhydrous stick composition paragraphs A-B, wherein the perfume raw materials are selected from the group consisting of: eugenyl formate; benzaldehyde; 2-hexen-1-yl acetate; alpha-methyl cinnamaldehyde; methyl phenylacetate; viridine; ethyl 2-phenylacetate; methyl hydrocinnamate; methyl cinnamate; 2-Phenyl-ethyl acetate; cinnamyl acetate; lilac acetaldehyde; 4-(p-Methoxyphenyl)-2-butanone; anethole; gamma-Octalactone; 3-phenyl propionaldehyde; cinnamic alcohol; cinnamic aldehyde; phenethyl formate; 3-phenyl propyl formate; isobutyl furylpropionate; styryl acetate; geranyl formate; 3-Hepten-1-ol; citronellol; trans-Geraniol; nerol; neral; melon heptenal; propyl mercaptan; 2-Propionylpyrrole; 5,6-Dimethyl-1-(1-methylethenyl)bicyclohept-5-ene-2-methanol; hydratopic alcohol; 3,4-Dimethoxyacetophenone; safranal; 2-Hydroxyacetophenone; cis-carveol, ocean propanal; Isosafrol; Indole; 2-Methylbenzothiazole; Ethyl vanillin; Vanillin; Methyl p-anisate; Benzyl propionate; 3-phenyl propyl acetate; phenyl acetaldehyde; p-Hydroxybenzaldehyde; para-anisaldehyde; Isoamyl acetate; Ethyl 3-methylthiopropionate; Methyl anthranilate; 1,2-Cyclopentanedione, 3-ethyl-; Syringaldehyde; furfuryl thioacetate; blackberry thiophenone; p-Cresyl acetate; linalool oxide (pyramid); Gerania; Parmanyl; Sorbinaldehyde; Pentyl 2-furyl ketone; m-Guaiacol; alpha-Methylcinnamic alcohol; Ethyl cyclohex-3-enecarboxylate; 2,4-Hexadienyl acetate; 4-Hydroxy-3-methylbenzaldehyde; Furan, 3-methyl-2-(3-methyl-2-butenyl)-; n-Pentyl acetoacetate; Ethyl 2-hexenoate; 2-Ethyl-4-methylthiazole; tropical thiazole; Trifernal; Coumarone; 2,4-Hexadienyl propionate;

Cyclopentyl mercaptan; 2-Methyl-2-butanethiol; trans-2-Methyl-2-pentenoic acid; 2-Hexyl-1,3-dioxolane; cis-3-Hepten-1-ol; 3-Hexenyl acetate; Trans,trans-2,4-Hexadien; methyl trans-cinnamate 99%; 4-Methyl-5-vinylthiazole; 2-Propylthiazole; (S),(−)-Perillaaldehyde; 2-(1-Methylpropyl)thiazole; (+)-p-menth-1-en-9-OL 97% (mixture of isomers); Isobutyl thiazole; trans-2-Heptenal; (1S)-(−)-cis-Verbenol; Anapear; alpha-Campholenic alcohol; Ethyl 2-mercaptopropionate; 2-Methylphenethyl alcohol; Methyl 4-phenylbutyrate; Allyl crotonate; Allyl butyrate; Benzyl lactate; Vanillin isobutyrate; perillaldehyde; Neryl Formate; Allyl methyl disulfide; Methyl propyl disulfide; 2-Cyclopenten-1-one, 2-hydroxy-3,4-dimethyl-; 3-Ethyl-2-hydroxy-2-cyclopenten-1-one; 2-Octenol-1; Tetrahydrofurfuryl butyrate; Allo-ocimenol; 7-Octene-1,6-diol, 3,7-dimethyl-; 3-Ethoxybenzaldehyde; 2-Ethylbenzaldehyde; 2-hexen-1-ol; Phenoxyethyl propionate; Nerolione; 7-Methylcoumarin; Butylacrolein; 2-Hexen-1-yl acetate; Ethyl phenoxyacetate; Ethyl trans-3-hexenoate; N-Acetyl methyl anthranilate; Ethyl trans-2-hexenoate; Vertoliff; (2E,6Z)-Nona-2,6-dien-1-ol; Ocimenol; 2,6-Dimethyl-1,5,7-octatrienol-3; p-Menth-1-ene-9-al; 2,4-Octadien-1-al; Propyl anthranilate; 2-Pentanoylfuran; 4-Ethyl-2-methylthiazole; Jasmolactone; cis-3-Hexenyl formate; 1-Octenol-3; 4,5-Dimethylthiazole; 4,4-Dimethyl-5-isopropyl-1,3-dioxolane; 1-Hexen-3-yl acetate; Furfuryl valerate; 2,6-Dimethyl-6-hepten-1-ol; cis-3-Hexenyl acetate; trans-3-Hexenyl acetate; 5-Ethyl-2-thiophenecarbaldehyde; 2-Phenyl-1(2) propenyl-1 ester; 3-Cyclohexene-1-ethanol, 4-methyl-beta-methylene-, (R)-; Furfuryl hexanoate; 3-methoxy cinnamaldehyde; 3-Acetyl-5-butyldihydro-2(3H)-furanone; Pyrazine, 3-butyl-2,5-dimethyl-; Methyl Heptenone; 2,5-Dimethylthiazole; (E)-anethol; Phenylethyl oxy-acetaldehyde; 3-Ethyl-2-hydroxy-4-methylcyclopent-2-en-1-one; (E,E)-2,4-heptadien-1-al; Cinnamic aldehyde dimethyl acetal; Campholene aldehyde; cis-4-Hexenal; 2-Hepten-4-one; 2-Octen-4-one; Verbenol; 4-Ethylbenzaldehyde; Piperitol; piperitenone; Isocoumarin; Lepidine; ethyl maltol; Butyroin; Hinokitiol; Pyrazine, 2-butyl-3,5-dimethyl-; cis-3, cis-6-nonadienol; trans-2-Hexenyl formate; Ethyl 2-methyl-4-pentenoate; 1-(4-Methylphenyl)ethanol; Perillyl alcohol; Cumic alcohol; citral; Benzyl acetoacetate; p-Methylhydrocinnamic aldehyde; 2,4-Dimethylthiazole; Acetaldehyde phenyl ethyl acetal; Canthoxal; Ethyl 3-mercaptopropionate; Raspberry ketone; 2-Methylthiophene; 3,6-Octadienal, 3,7-dimethyl-; 2,4-Octadienal; Cinnamaldehyde ethylene glycol acetal; trans-3, cis-6-nonadienol; 2-Heptenal, (2Z)-; Methyl furfuryl disulfide; o-Acetylanisole; Lavandulol; 3-Methylacetophenone; p-Tolyl alcohol; Furfuryl thiopropionate; 2-Mercaptomethylpyrazine; 2,4-Heptadienal; cis-iso-Eugenol; S-Ethyl benzothioate; trans-Isoeugenol; Methyl 2-nitrobenzoate; Methyl o-methoxybenzoate; Guaiacyl acetate; 3-Methylthiophene; cis-4-Hepten-1-ol; beta-Phenoxy ethyl acetate; cis-3-Hexenyl lactate; meta-tolyl aldehyde; 4-(2-Furyl)-3-buten-2-one; Dimethyl disulfide; Cyclopentyl isobutyrate; Phenylacetaldehyde diethyl acetal; tetrahydrofurfuryl propionate; 2,5-Dimethylthiophene; Ethyl 2-methoxybenzyl ether; p-Methoxy-alpha-methyl cinnamaldehyde; Geranyl oxy-acetaldehyde; Ethyl (p-tolyloxy)acetate; Trans-2-Hexenal; cis-4-Heptenal; 3-Mercapto-2-pentanone; 3,5,6-Trimethyl-3-cyclohexene-1-carbaldehyde; Floralol; 2,4-Dimethyl-3-cyclohexene-1-methanol; trans-2-Hexenal diethyl acetal; 3,6-ivy carbaldehyde; p-Methyl phenoxy acetaldehyde; (Z)-3-hexen-1-al; Dimethyl cyclohexene carboxaldehyde; 2,4-Dimethyl-3-Cyclohexene-1-carboxaldehyde; cis-3-Hexenyl pyruvate; 3,5-ivy carbaldehyde; delta-Octalactone; Methyl benzyl disulfide; 1-Phenylbutan-2-ol; Ethyl 2-methylbutyrate; Methyl mercaptan; Allyl anthranilate; Allyl tiglate; Ethanethiol; dimethyl sulfide 2-Propanethiol; (−)-Citronellol; Anisyl propionate; tert-Butyl mercaptan; 2,4-Pentadienal; 3,6-Nonadien-1-ol; Benzaldehyde diethyl acetal; 2-Thienyl mercaptan; 4-(p-Tolyl)-2-butanone; Isoeugenyl formate; 2,6-Nonadien-1-ol; 2-Methoxy-4-vinylphenol; p-Menth-8-en-3-ol; filbert heptenone; Gardamide; Dimethyl anthranilate; Allyl mercaptan; Ethyl anthranilate; cinnamon acrolein; Vanillin acetate; Isopulegol; Salicylaldehyde; Guaiacol; Hydratropaldehyde dimethyl acetal; Coumarin (Z)-2-hexen-1-ol; (E)-2-hexen-1-ol; cis-3-Hexen-1-ol; Methyl isoeugenol; Isoeugenyl acetate; 2-phenyl propionaldehyde; 1-Phenyl-1-propanol; Methyl benzoate; Ethyl benzoate; Citronitrile; Styrallyl acetate; Butanoic acid, 2-methyl-, 2-hexenyl ester, (E)-; Vanitrope; 2-Methylindole; Eugenol; and a combination thereof.

D. The anhydrous stick composition of paragraphs A-B, wherein the perfume raw materials are selected from the group consisting of: beta gamma hexanol; cis 3 hexenyl acetate; ethyl-2-methyl butyrate; amyl-acetate; vanillin; anethole; methyl isoeugenol; guaiacol; floralol; 2,6-nonadien-1-ol; coumarin; and a combination thereof.

E. The anhydrous stick composition of any of paragraphs A-B, wherein the perfume raw materials comprise dimethyl anthranilate; iso-eugenyl acetate; canthoxal; 3,6-nonadien-1-ol, triplal; or a combination thereof.

F. The anhydrous stick composition of any of paragraphs A-B, wherein the perfume raw materials comprise ethyl-2-methyl butyrate; beta gamma hexanol; iso amyl acetate; amyl acetate; cis-3-hexenyl acetate; gamma-octalactone; ethyl vanillin; vanillin; benzaldehyde; or a combination thereof.

G. The anhydrous stick composition of any of paragraphs A-F, wherein the 10% or more of the perfume raw materials also have an Odor Detection Threshold of about 7 or more -log molar concentration.

H. The anhydrous stick composition of any of paragraphs A-G, wherein 10% or more of the perfume raw materials also have an Odor Detection Threshold of about 7 to about 11.5-log molar concentration.

I. The anhydrous stick composition of any of paragraphs A-H, wherein about 20% to about 100%, by weight of the perfume, of the perfume raw materials have: a complex stability constant of about 3.0 or less, a C log P of about 2.5 or less; and a weight average molecular weight of about 200 Daltons or less.

J. The anhydrous stick composition of any of paragraphs A-I, wherein about 50% to about 100%, by weight of the perfume, of the perfume raw materials have: a complex stability constant of about −2.0 to about 3, a C log P of about 2.5 or less; and a weight average molecular weight of about 200 Daltons or less.

K. The anhydrous stick composition of any of paragraphs A-J, wherein the perfume raw materials have a complex stability constant of about −1.5 to about 2.5.

L. The anhydrous stick composition of any of paragraphs A-K, wherein the perfume raw materials have a C log P of about 2.0 or less.

M. The anhydrous stick composition of any of paragraphs A-L, wherein the perfume raw materials have a weight average molecular weight of about 180 Daltons or less.

N. The anhydrous stick composition of any of paragraphs A-M, wherein the cyclodextrin comprises an alpha-cyclodextrin, a beta-cyclodextrin, a gamma-cyclodextrin, or a combination thereof O. The anhydrous stick composition of any of paragraphs A-N, wherein the cyclodextrin comprises hydroxypropyl alpha-cyclodextrin, hydroxypropyl beta-cyclodextrin, methylated-alpha-cyclodextrin, methylated-beta-cyclodextrin, or a combination thereof.

P. The anhydrous stick composition of any of paragraphs A-O, wherein the percent of the perfume that is complexed with the cyclodextrin is greater than about 75%.

Q. The anhydrous stick composition of any of paragraphs A-P, wherein the percent of the perfume that is complexed with the cyclodextrin is greater than about 95%.

R. The anhydrous stick composition of any of paragraphs A-Q, wherein the 10% or more of the perfume raw materials also have an Odor Detection Threshold of about 7 or more -log molar concentration.

S. The anhydrous stick composition of any of paragraphs A-Q, wherein 10% or more of the perfume raw materials also have an Odor Detection Threshold of about 7 to about 11.5-log molar concentration.

T. The anhydrous stick composition of any of paragraphs A-S, wherein about 20% to about 100%, by weight of the perfume, of the perfume raw materials have: a complex stability constant of about 3.0 or less, a C log P of about 2.5 or less; and a weight average molecular weight of about 200 Daltons or less.

U. The anhydrous stick composition of any of paragraphs A-T, wherein about 50% to about 100%, by weight of the perfume, of the perfume raw materials have: a complex stability constant of about 0 to about 3, a C log P of about 2.5 or less; and a weight average molecular weight of about 200 Daltons or less.

V. The anhydrous stick composition of any of paragraphs A-U, wherein the perfume raw materials have a complex stability constant of about −1.5 to about 2.5.

W. The anhydrous stick composition of any of paragraphs A-V, wherein the perfume raw materials have a C log P of about 2.0 or less.

X. The anhydrous stick composition of any of paragraphs A-W, wherein the perfume raw materials have a weight average molecular weight of about 180 Daltons or less.

Y. An anhydrous stick composition, comprising a deodorant active, an antiperspirant active, or a combination thereof a carrier; a structurant; and a cyclodextrin complex, comprising perfume raw materials and wherein 20% or more, by weight of the perfume, of the perfume raw materials, are selected from the group consisting of: ethyl-2-methyl butyrate; beta gamma hexanol; iso amyl acetate; amyl acetate; cis-3-hexenyl acetate; gamma-octalactone; ethyl vanillin; vanillin; benzaldehyde; dimethyl anthranilate; iso-eugenyl acetate; canthoxal; 3,6-nonadien-1-ol, triplal; and combinations thereof Z. The anhydrous stick composition of paragraph Y, wherein the perfume raw materials are selected from the group consisting of ethyl-2-methyl butyrate; beta gamma hexanol; iso amyl acetate; amyl acetate; cis-3-hexenyl acetate; gamma-octalactone; ethyl vanillin; vanillin; benzaldehyde; and combinations thereof.

AA. The anhydrous stick composition of paragraph Y, wherein the perfume raw materials are selected from the group consisting of: dimethyl anthranilate; iso-eugenyl acetate; canthoxal; 3,6-nonadien-1-ol, triplal; and combinations thereof.

BB. The anhydrous stick composition of any of paragraphs Y-AA, wherein about 20% to about 100%, by weight of the perfume, of the perfume raw materials have: a complex stability constant of about 3.0 or less, a C log P of about 2.5 or less; and a weight average molecular weight of about 200 Daltons or less.

CC. The anhydrous stick composition of any of paragraphs Y-BB, wherein about 50% to about 100%, by weight of the perfume, of the perfume raw materials have: a complex stability constant of about 0 to about 3, a C log P of about 2.5 or less; and a weight average molecular weight of about 200 Daltons or less.

DD. The anhydrous stick composition of any of paragraphs Y-CC, wherein about 50% to about 100% of the perfume raw materials have a complex stability constant of about −1.5 to about 2.5.

EE. The anhydrous stick composition of any of paragraphs Y-DD, wherein about 50% to about 100% of the perfume raw materials have a C log P of about 2.0 or less.

FF. The anhydrous stick composition of any of paragraphs Y-EE, wherein about 20% to about 100% of the perfume raw materials have a weight average molecular weight of about 180 Daltons or less.

GG. The anhydrous stick composition of any of paragraphs Y-FF, wherein the perfume is part of a cyclodextrin complex.

HH. The anhydrous stick composition of any of paragraphs Y-GG, wherein the cyclodextrin comprises an alpha-cyclodextrin, a beta-cyclodextrin, a gamma-cyclodextrin, or a combination thereof.

II. The anhydrous stick composition of any of paragraphs Y-HH, wherein the cyclodextrin comprises hydroxypropyl alpha-cyclodextrin, hydroxypropyl beta-cyclodextrin, methylated-alpha-cyclodextrin, methylated-beta-cyclodextrin, or a combination thereof.

JJ. The anhydrous stick composition of any of paragraphs Y-II, wherein the percent of the perfume that is complexed with the cyclodextrin is greater than about 75%.

KK. The anhydrous stick composition of any of paragraphs Y-JJ, wherein the percent of the perfume that is complexed with the cyclodextrin is greater than about 95%.

LL. The anhydrous stick composition of any of paragraphs Y-KK, wherein the cyclodextrin comprises beta-cyclodextrin.

EXAMPLES

Exemplary perfume compositions in accordance with the invention can include:

| Material | % by weight of perfume composition |
| --- | --- |
| Cis-3-hexen-1-ol | 5-50% |
| Cis-3-hexenyl acetate | 5-50% |
| Ethyl 2-methylbutyrate | 5-50% |
| Isoamyl acetate | 5-50% |
| Vanillin | 5-50% |

Additional information about the perfume raw materials in the example can be found in the table below:

| CAS Number | Name | cLogP | Weight average molecular weight (Dalton) | Odor Detection threshold (−log molar concentration) | Cyclodextrin stability constant (log K) |
|---|---|---|---|---|---|
| 123-92-2 | Isoamyl acetate | 1.87 | 130 | 7.12 | 0.33 |
| 121-33-5 | Vanillin | 1.04 | 152 | 9.93 | 1.36 |
| 7452-79-1 | Ethyl 2-methylbutyrate | 1.91 | 130 | 7.27 | 0.75 |
| 928-96-1 | Cis-3-hexen-1-ol | 1.3 | 100 | 8.06 | 1.06 |
| 3681-71-8 | Cis-3-hexenyl acetate | 2.18 | 142 | 8.16 | 0.48 |

The perfume composition can be made by blending all of the perfume raw materials together until a homogenous solution is formed.

This exemplary composition can then be formed into a cyclodextrin complex by mixing 10 parts cyclodextrin with 10 (or more) parts water, and 1 part (or less) of the perfume composition. After the mixing, the slurry will be more viscous than at the start of mixing—the change in viscosity is believed to be due to the formation of the cyclodextrin perfume complex. The mixture is then dried (or spray dried) to remove the water and leave the cyclodextrin and perfume complex as a powder.

Exemplary Solid Stick and Soft Solid Antiperspirant Compositions

| Raw Materials | Inventive Solid Stick Formula #1 Weight % | Inventive Soft Solid Formula #1 Weight % |
|---|---|---|
| Aluminum Zirconium Tetrahlorohydrex Gly | 25.6 | |
| Aluminum Zirconium Trihlorohydrex Gly | | 26.49 |
| Cyclomethicone, DC245, SF1202 | 30.45 | 55.385 |
| Stearyl Alcohol | 13.75 | |
| Syncrowax HRC | | 4.5 |
| Syncrowax HGL-C | | 1.125 |
| Petrolatum | 3 | 3 |
| PPG-14 butyl ether | 2 | 0.5 |
| Dimethicone 50 cst | 5 | |
| Dimethicone 10 cst | | 5 |
| Hydrogenated Castor Oil | 2.5 | |
| C20-40 pareth-10 ethoxylate | 1 | |
| Behenyl Alcohol | 0.2 | |
| Mineral Oil | 8 | |
| Talc | 3 | |
| beta - Cyclodextrin perfume complex | 3 | 3 |
| Perfume | 2.5 | 1 |
| Total | 100 | 100 |

Inventive Solid Stick Formulation 1 can be prepared by a split stream process. In the hot stream tank, all of the waxes and oils (except as noted otherwise), surfactant (C20-40 pareth 10 ethoxylate) and other emollients (C12-15 Alkyl benzoate, petrolatum, etc.) and a lesser portion of the cylopentasilaxane are adding into one tank mixed and heated to 88° C. to melt the waxes. In the cold stream tank, all of the powders (active, talc, cyclodextrin perfume complex), free perfume, PPG-14 butyl ether, and a greater portion of the cyclopentasiloxane are added and mixed and maintained at a temperature less than 50° C. Once each of the hot and cold streams are adequately mixed so they are homogenous, each of the process streams are simultaneously fed into a static mixer where they combine for about 5 seconds or less, to ensure a homogenous product while minimizing the mix time above the wax crystallization temperature. The product then exits the static mixer into individual canisters where it is allowed to cool to room temperature.

Inventive Soft Solid Formulation 1 can be prepared by a split stream process. In the hot stream tank, all of the waxes and oils (unless noted otherwise), and other emollients (dimethicone, petrolatum) and a lesser portion of the cylopentasilaxane are adding into one tank mixed and heated to 88° C. to melt the waxes. In the cold stream tank, all of the powders (active, beta cyclodextrin perfume complex), free perfume, and a greater portion of the cyclopentasiloxane are added and mixed and maintained at a temperature less than 50° C. Once each of the hot and cold streams are adequately mixed so they are homogenous, each of the process streams are simultaneously fed into a static mixer where they combine for about 5 seconds or less, to ensure a homogenous product while minimizing the mix time above the wax crystallization temperature. The product then exits the static mixer into individual canisters where it is allowed to cool to room temperature.

In Vitro Perfume Release Method
Released Perfume (RP) Sample

About 500 milligrams of a cyclodextrin perfume complex is weighed into a glass scintillation vial. About 1 milliliter of water is added to the vial. The vial is then capped tightly and vortexed for about 30 seconds to create a slurry. The RP sample is then placed into a 37 degrees Celsius oven to incubate for 4 hours. The sample vial is removed from the oven and allowed to cool to room temperature. 10 milliliters of hexane is then added to the vial. The vial is capped tightly and mixed by hand shaking for about 10 seconds and then mixed on high speed with a vortex mixer for about 30 seconds to extract perfume components liberated by the water incubation step. After allowing solids to settle, an aliquot of the sample is transferred to a 2 milliliter autosampler vial for analysis.

Total Perfume (TP) Sample

Another 500 milligrams of the same cyclodextrin perfume complex used to create the RP sample is weighed into a scintillation vial. About 10 milliliters of acetone is added to the vial. This sample is then capped tightly and vortexed for about 30 seconds to disperse the sample. The total sample is then placed into a 70 degrees Celsius oven for 4 hours. The sample is removed from the oven and allowed to cool to room temperature. After allowing solids to settle, an aliquot of the sample is transferred to a 2 milliliter autosampler vial for analysis.

Analysis

The RP and TP samples are analyzed using liquid injection gas chromatography with a mass selective detector. The injection port is heated to 270 degrees Celsius and operated in split mode with a split ratio of about 20:1. The carrier gas is helium and delivered at a constant flowrate of about 1.2 milliliters per minute. The oven temperature is ramped from an initial temperature of 50 degrees Celsius to a final temperature of 250 degrees Celsius at a rate of 10 degrees Celsius per minute. The final temperature is held for 2 minutes. The mass selective detector is operated in scanning mode and perfume components are identified using NIST mass spectral library searching. The chromatogram from the TP sample is used to identify a specific mass to charge ratio for each perfume component and extracted ion peak areas for each perfume component are obtained. The RP chromatogram is correspondingly processed.

Results Calculation

Individual perfume component peak areas per unit of sample weight from the RP sample are divided by the corresponding peak areas per unit of sample weight from the TP sample. The resulting ratio is multiplied by 100 to calculate a release percentage for each individual perfume material. The release percentages from all perfume components are averaged to calculate a composite release value for a given complex sample.

Finished Product Testing

Where the ability to test the cyclodextrin perfume complex itself is not available, one can test for perfume release from a cyclodextrin perfume complex contained in a finished product as set out below.

Finished Product Testing

In duplicate, 50 milligrams of finished product personal aerosol composition is weighed onto a 1.5×3 centimeters strip of aerosol testing paper manufactured by Orlandi. The samples are allowed to sit on a laboratory benchtop for at least 72 hours to allow volatile matrix components and parent perfume to evaporate. One of the treated strips is transferred—in its dry condition—to a 20 milliliter headspace vial and capped tightly. The other sample strip is sprayed with a fine mist of about 20 milligrams of water and then transferred into a separate 20 milliliter headspace vial and capped tightly. The headspace sample vials are allowed to equilibrate for about 2 hours and then transferred to the gas chromatograph for analysis.

Analysis

The samples are analyzed using headspace solid phase microextraction (SPME) gas chromatography with a mass selective detector. The headspace samples are incubated at about 30 degrees Celsius for 10 minutes. The headspace is then sampled using a Supelco 50/30 μm divinylbenzene/Carboxen on polydimethylsiloxane 1 centimeter SPME fiber for 1 minute. The autosampler desorbs the fiber in the injection port, which is heated to 270 degrees Celsius and operated in splitless mode. The carrier gas is helium and delivered at a constant flowrate of about 1.2 milliliters per minute. The oven temperature is ramped from an initial temperature of 50 to a final temperature of 250 degrees Celsius at a rate of 10 degrees Celsius per minute. The final temperature is held for 2 minutes. The mass selective detector is operated in scanning mode and perfume components are identified using NIST mass spectral library searching.

Chromatogram Evaluation

The total ion chromatogram from the wetted sample is overlaid with the total ion chromatogram from the dry sample. Chromatographic peaks that are observed only from the wetted sample are a result of perfume components being released from a perfume delivery technology that is activated by water. These perfume components can then be identified using a mass spectral library such as NIST.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An anhydrous stick composition, comprising:
   a) a deodorant active, an antiperspirant active, or a combination thereof;
   b) a carrier;
   c) a structurant comprising stearyl alcohol; and
   d) a cyclodextrin perfume complex, comprising cyclodextrin and a perfume, wherein the perfume comprises perfume raw materials and wherein from about 40% to 50%, by weight of the perfume, of the perfume raw materials have: a complex stability constant of about 3.0 or less, a C log P of about 2.5 or less; and
   a weight average molecular weight of about 200 Daltons or less.

2. The anhydrous stick composition of claim 1, wherein the cyclodextrin complex stability constant (log k) is from about −2.0 to about 2.5.

3. The anhydrous stick composition of claim 1, wherein the perfume raw materials are selected from the group consisting of: beta gamma hexanol;
   cis 3 hexenyl acetate; ethyl-2-methyl butyrate; amylacetate; vanillin; anethole; methyl isoeugenol; guaiacol; floralol; 2,6-nonadien-l-ol; coumarin; and a combination thereof.

4. The anhydrous stick composition of any of claim 1, wherein the perfume raw materials comprise dimethyl anthranilate;
   iso-eugenyl acetate; canthoxal; 3,6-nonadien-1-ol, triplal; or a combination thereof.

5. The anhydrous stick composition of claim 1, wherein the perfume raw materials comprise ethyl-2-methyl butyrate; beta gamma hexanol; iso amyl acetate; amyl acetate; cis-3-hexenyl acetate; gamma-octalactone; ethyl vanillin;
   vanillin; benzaldehyde; or a combination thereof.

6. The anhydrous stick composition of claim 1, wherein 10% or more of the perfume raw materials also have an Odor Detection Threshold of about 7 to about 11.5—log molar concentration.

7. The anhydrous stick composition of claim 1, wherein the perfume raw materials have a complex stability constant of about −1.5 to about 2.5.

8. The anhydrous stick composition of claim 1, wherein the perfume raw materials have a C log P of about 2.0 or less.

9. The anhydrous stick composition of claim 1, wherein the perfume raw materials have a weight average molecular weight of about 180 Daltons or less.

10. The anhydrous stick composition of claim 1, wherein the cyclodextrin comprises hydroxypropyl alpha-cyclodextrin, hydroxypropyl beta-cyclodextrin, methylated-alpha-cyclodextrin, methylated-beta-cyclodextrin, or a combination thereof.

11. The anhydrous stick composition of claim 1, wherein the percent of the perfume that is complexed with the cyclodextrin is greater than about 75%.

12. An anhydrous stick composition, comprising: deodorant active, an antiperspirant active, or a combination thereof; a carrier; a structurant; and a cyclodextrin perfume complex, comprising cyclodextrin and a perfume, wherein the perfume comprises perfume raw materials wherein from about 40% to 70%, by weight of the perfume, of the perfume raw materials, are selected from the group consisting of:
    ethyl-2-methyl butyrate; beta gamma hexanol; iso amyl acetate; amyl acetate; cis-3-hexenyl acetate; gamma-octalactone; ethyl vanillin; vanillin; benzaldehyde; dimethyl anthranilate; iso-eugenyl acetate; canthoxal; 3,6-nonadien-1-ol, triplal; and
    combinations thereof.

13. The anhydrous stick composition of claim 12, wherein the perfume raw materials are selected from the group consisting of: dimethyl anthranilate; iso-eugenyl acetate; canthoxal; 3,6-nonadien-1-ol, triplal; and
    combinations thereof.

14. The anhydrous stick composition of claim 12, wherein about 20% to about 100%, by weight of the perfume, of the perfume raw materials have: a complex stability constant of about 3.0 or less, a C log P of about 2.5 or less; and a weight average molecular weight of about 200 Daltons or less.

15. The anhydrous stick composition of claim 12, wherein about 50% to about 100% of the perfume raw materials have a complex stability constant of about −1.5 to about 2.5.

16. The anhydrous stick composition of claim 12, wherein about 50% to about 100% of the perfume raw materials have a C log P of about 2.0 or less.

17. The anhydrous stick composition of claim 12, wherein about 20% to about 100% of the perfume raw materials have a weight average molecular weight of about 180 Daltons or less.

18. The anhydrous stick composition of claim 12, wherein the percent of the perfume that is complexed with the cyclodextrin is greater than about 75%.

19. The anhydrous stick composition of claim 12, wherein the cyclodextrin comprises beta-cyclodextrin.

* * * * *